(12) United States Patent
Lewis et al.

(10) Patent No.: US 8,629,902 B2
(45) Date of Patent: Jan. 14, 2014

(54) COORDINATE FUSION AND THICKNESS CALIBRATION FOR SEMICONDUCTOR WAFER EDGE INSPECTION

(75) Inventors: Isabella T. Lewis, San Jose, CA (US); Tim S. Wihl, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 600 days.

(21) Appl. No.: 12/902,673

(22) Filed: Oct. 12, 2010

(65) Prior Publication Data
US 2012/0086796 A1   Apr. 12, 2012

(51) Int. Cl.
*H04N 7/18*   (2006.01)
(52) U.S. Cl.
USPC .......................................... 348/87; 356/237.4
(58) Field of Classification Search
None
See application file for complete search history.

(56) References Cited

U.S. PATENT DOCUMENTS

| | | | |
|---|---|---|---|
| 2003/0135302 A1* | 7/2003 | Hung et al. | 700/245 |
| 2004/0207836 A1* | 10/2004 | Chhibber et al. | 356/237.4 |
| 2004/0258514 A1* | 12/2004 | Raaijmakers | 414/935 |
| 2009/0130784 A1 | 5/2009 | Michelsson et al. | |

FOREIGN PATENT DOCUMENTS

| | | | |
|---|---|---|---|
| JP | 2008298546 A | 12/2008 | |
| JP | 2009156686 A | 7/2009 | |
| JP | 2009222516 A | 10/2009 | |
| KR | 10-2008-0078812 A | 8/2008 | |

* cited by examiner

*Primary Examiner* — Sath V Perungavoor
*Assistant Examiner* — Dakshesh Parikh
(74) *Attorney, Agent, or Firm* — Suiter Swantz pc llo

(57) ABSTRACT

A system may include a support configured to rotatably support a wafer. The system may also include an imager for generating an image of a wafer, where the image includes a first coordinate reference. The system may also include a profiler for generating a profile of the wafer, where the profile includes a second coordinate reference. The system may further include control programming for locating at least one structural feature of an edge of the wafer recognizable by both the imager and the profiler for allowing the first coordinate reference to be mapped to the second coordinate reference. The wafer used in calibration may have discrete edge features detectable in an edge imager and in an edge profiler.

20 Claims, 36 Drawing Sheets

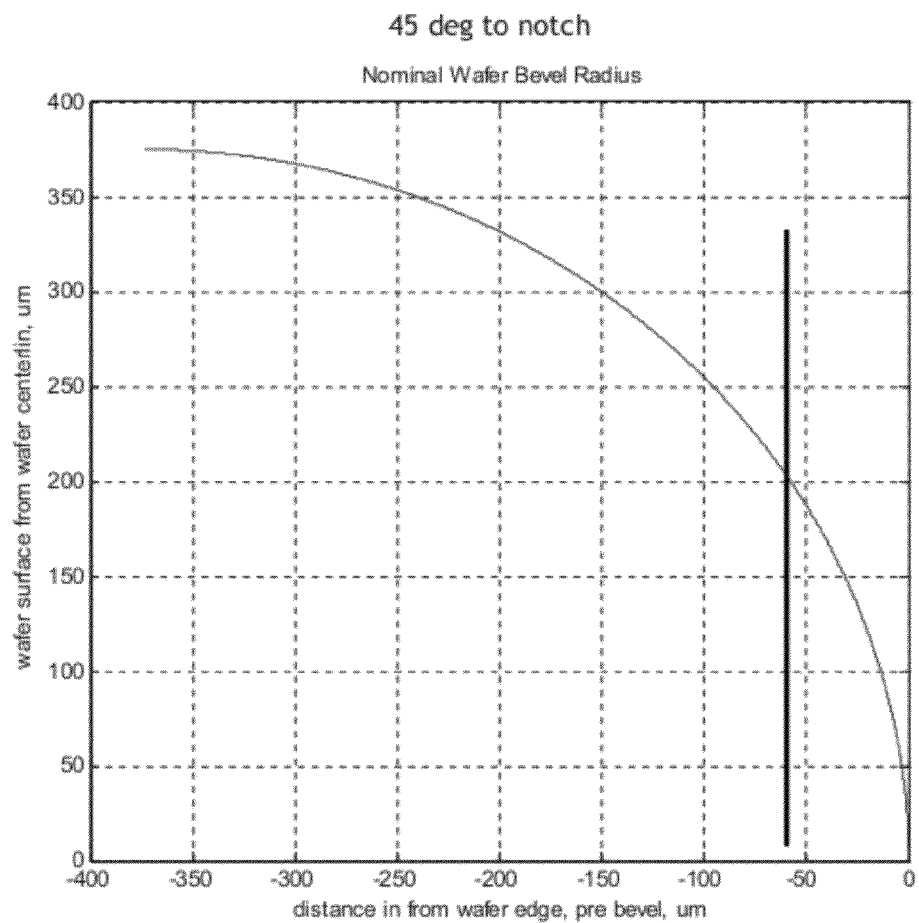
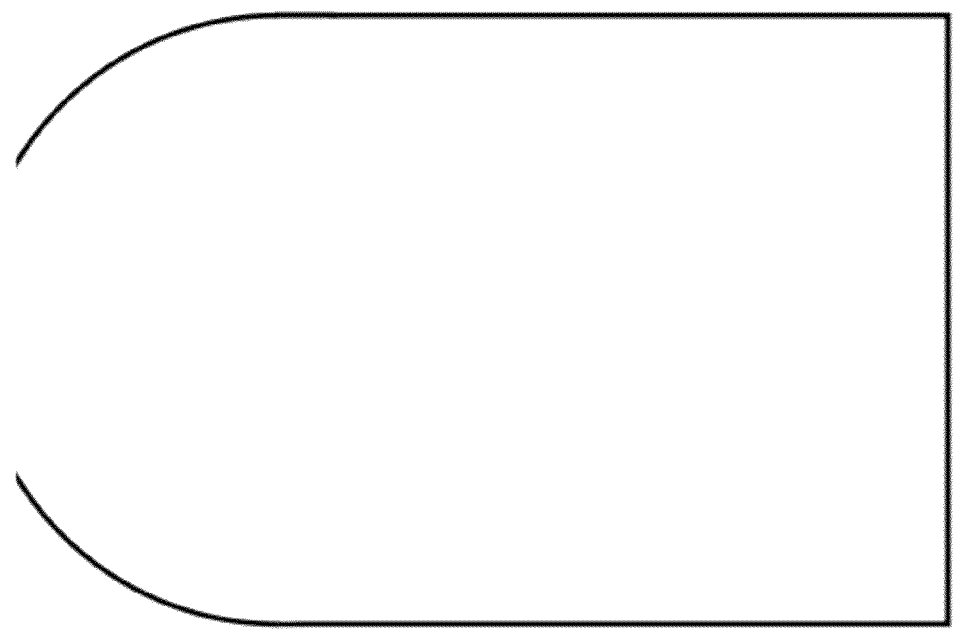
FIG. 21

DETAIL C

DETAIL A

DETAIL B

COORDINATE FUSION AND THICKNESS CALIBRATION FOR SEMICONDUCTOR WAFER EDGE INSPECTION

TECHNICAL FIELD

The present disclosure generally relates to the field of semiconductor fabrication, and more particularly to a method and system for calibrating an imager and a profiler.

BACKGROUND

Wafers made from semiconductor materials may be utilized in the fabrication of integrated circuits. Such wafers may serve as substrates for microelectronic devices, which may be included in and on a wafer. Such wafers may undergo such processes as doping, etching, deposition of material, and/or photolithographic patterning.

SUMMARY

A system may include a support configured to rotatably support a wafer. The system may also include an imager for generating an image by scanning a first region on an edge of the wafer, a second region on a first side of the wafer proximal to the edge of the wafer, and a third region on a second side of the wafer proximal to the edge of the wafer. The image includes a first coordinate reference. The system may also include a profiler for generating a profile by projecting at least nominally collimated light in a direction at least substantially parallel to the first side of the wafer and the second side of the wafer. The at least nominally collimated light may be projected past the edge of the wafer. The profile includes a second coordinate reference. The system may further include control programming for locating at least one structural feature of the edge of the wafer recognizable by both the imager and the profiler for allowing the first coordinate reference to be mapped to the second coordinate reference.

A method may include rotatably supporting a wafer. The method may also include generating an image of the wafer by scanning a first region on an edge of the wafer, a second region on a first side of the wafer proximal to the edge of the wafer, and a third region on a second side of the wafer proximal to the edge of the wafer. The image includes a first coordinate reference. The method may also include generating a profile of the wafer by projecting at least nominally collimated light in a direction at least substantially parallel to the first side of the wafer and the second side of the wafer. The at least nominally collimated light may be projected past the edge of the wafer. The profile includes a second coordinate reference. The method may further include locating at least one structural feature of the edge of the wafer on both the image and the profile. The method may also include mapping the first coordinate reference to the second coordinate reference utilizing the at least one structural feature of the edge of the wafer.

A system may include a support for rotatably supporting a wafer having a discontinuous edge. The system may also include an imager for generating an image of the wafer by scanning a first region on an edge of the wafer, a second region on a first side of the wafer proximal to the edge of the wafer, and a third region on a second side of the wafer proximal to the edge of the wafer, where the image generated by the imager includes a first coordinate system. The system may also include a profiler for generating a profile of the wafer by projecting at least nominally collimated light in a direction at least substantially parallel to the first side of the wafer and the second side of the wafer. The at least nominally collimated light may be projected past the edge of the wafer, where the profile generated by the profiler includes a second coordinate system. The system may further include control programming for locating at least one structural feature of the discontinuous edge of the wafer recognizable by both the imager and the profiler for allowing the first coordinate system to be mapped to the second coordinate system.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which:

FIGS. 21 through 23 illustrate various degrees to notch the calibration wafer illustrated in FIG. 18;

DETAILED DESCRIPTION

Figure 1:
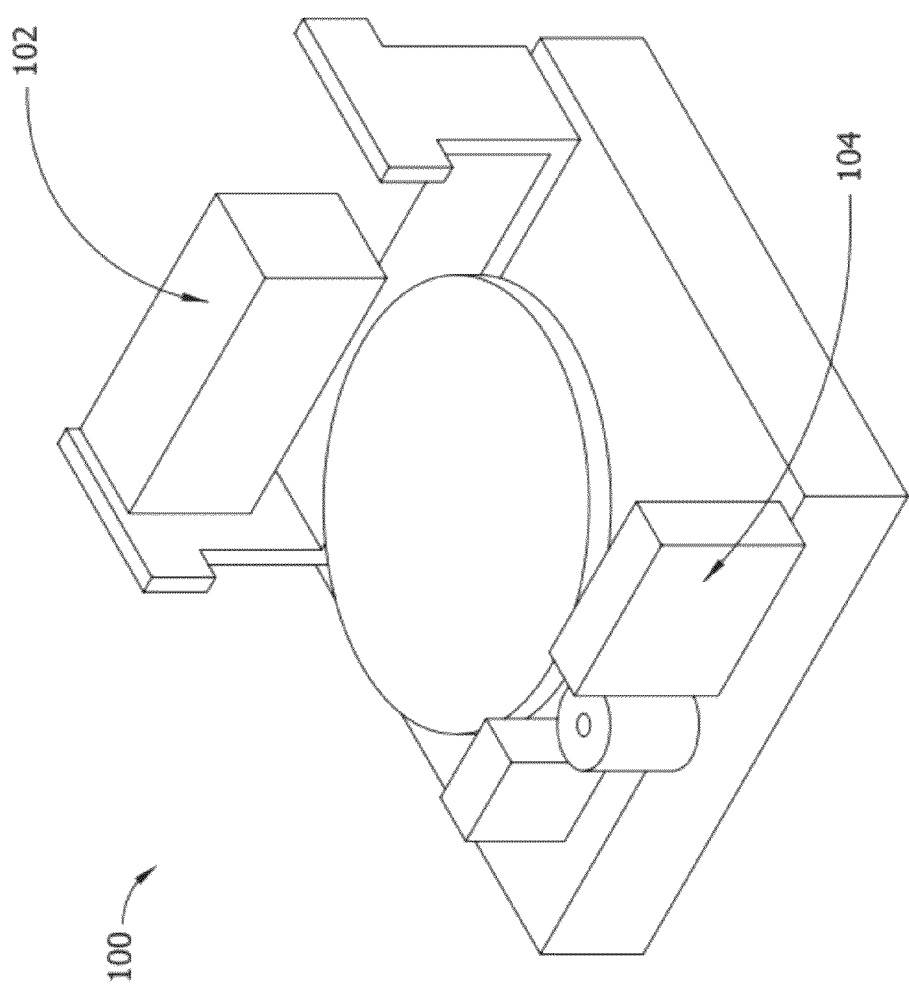
FIG. 1 is a perspective view illustrating a system for generating an image and a profile of a semiconductor wafer, where the image includes a first coordinate reference and the profile includes a second coordinate reference, and where the system is configured for mapping the first coordinate reference to the second coordinate reference.

Reference will now be made in detail to the subject matter disclosed, which is illustrated in the accompanying drawings.

Referring generally to FIGS. 1 through 49, a system 100 for generating an image of a wafer and generating a profile of the wafer, where the image includes at least a first coordinate reference and the profile includes at least a second coordinate reference, is described in accordance with the present disclosure. In embodiments, the system 100 is configured for mapping the first coordinate reference to the second coordinate reference. The system 100 includes an edge imaging system 102 and a shadow/edge profiler system 104.

The edge imaging system 102 may utilize a laser spot to scan an image around at the edge of a wafer (e.g., calibration wafer 106, which may be constructed from a semiconductor material or another material). In embodiments, the area scanned may include a zone on the top and bottom. The image produced by the edge imaging system 102 may then be utilized to identify "defects" (which may include, but are not limited to, dirt, film blisters, and/or film voids). The edge imaging system 102 may also be utilized to find the "edge" of a film bead, such as would have been created by a semiconductor manufacturer in the process of Edge Bead Removal (EBR).

In some instances, it may be desirable to determine the EBR physical location (e.g., in terms of a vertical or Z direction) as compared to the top of the semiconductor wafer. This may be referred to as the "Zcut height." Because the edge imaging system 102 images perpendicular to the wafer edge, additional depth information may be required to create a profile of the wafer edge, which may be necessary for reporting an accurate Zcut height. Thus, it is often desirable to provide for imaging across a wafer to gather accurate Z-dimension information. Accordingly, a shadow/edge profiler system 104 may be included in addition to the edge imaging system 102. In embodiments, the shadow/edge profiler system 104 projects nominally collimated light in a direction parallel to the wafer top and bottom surfaces and past the edge of the wafer. The apex of the wafer edge may be reimaged onto a camera. Utilizing the shadow/edge profiler system 104, sub-micrometer location of the wafer bevel may be achieved.

The image produced by the edge imaging system 102 may include one or more coordinate references (e.g., a Z-dimension measurement). Further, the profile produced by the shadow/edge profiler system 104 may include other coordinate references (e.g., Z-dimension measurements). In order to map the coordinate references between the two measuring devices (e.g., the edge imaging system 102 and the shadow/edge profiler system 104), both systems may be utilized to measure a similar structure. For example, a structure may be chosen that has at least one structural feature recognizable by both the edge imaging system 102 and the shadow/edge profiler system 104, allowing a first coordinate reference for the edge imaging system 102 to be mapped to a second coordinate reference for the shadow/edge profiler system 104. In some embodiments, in order to obtain the Zcut height of the EBR, the two coordinate systems utilized by the edge imaging system 102 and the shadow/edge profiler system 104 may need to be boresighted. It should be noted that since the shadow/edge profiler system 104 creates and/or reimages a shadow, only features protruding from a wafer may be recognizable by the shadow/edge profiler system 104. In contrast, the edge imaging system 102 may be capable of recognizing various perturbations, including protruding and/or incised perturbations. Additionally, the edge imaging system 102 may be capable of recognizing contrast printed on the surface of a wafer.

Referring generally to FIGS. 2 through 24, a calibration wafer 106 is described in accordance with the present disclosure. In embodiments, the calibration wafer 106 may be constructed from a semiconductor/substrate material, such as a single crystal silicon material, a metal material (e.g., aluminum), or the like. In some embodiments, a silicon may be doped with a material such as boron, phosphorus, arsenic, or antimony. In other embodiments, doping is not utilized. In embodiments, the simple wafer structure of the calibration wafer 106 may allow for normal loading and handling techniques during calibration. Further, the calibration wafer 106 may be cleanable, may be non-destructive during calibration, and may include well-established edges resulting in a small point error. Further, a large number of points around the periphery of the wafer may provide for a large amount of data checking.

For example, the calibration wafer 106 may include a discontinuous edge 108 finished on a wafer bevel that is viewable with high accuracy (e.g., the calibration wafer 106 profile may be accurately viewed by both an edge imaging system 102 and a shadow/edge profiler system 104). In embodiments, the calibration wafer 106 may include multiple discontinuous edges. In one embodiment, the discontinuous edge 108 of the calibration wafer 106 may include facet cuts to create calibration targets for the cameras of the edge imaging system 102 and/or the shadow/edge profiler system 104. In another embodiment, the calibration wafer 106 may include a single facet cut to create calibration targets for the edge imaging system 102 and/or the shadow/edge profiler system 104. In another embodiment, the facets may be cut concentrically from the wafer center (to yield constant length features) or may be cut eccentrically (to create varying length facet features).

Figure 3:
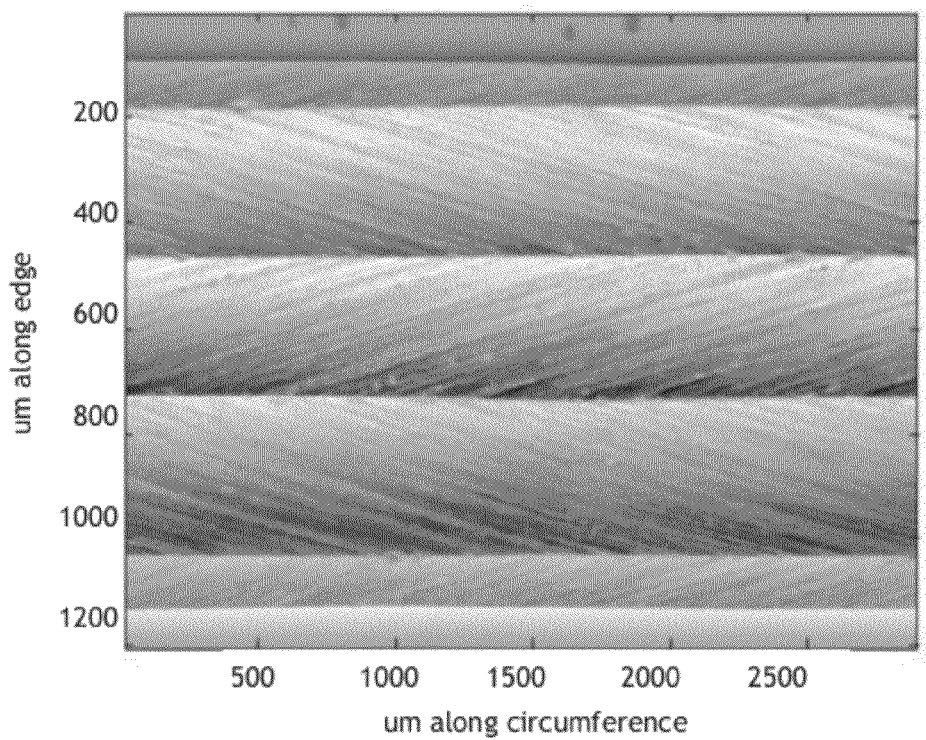
FIG. 3 is a partial end elevation view illustrating a calibration wafer as imaged by an edge imaging system.
Figure 4:
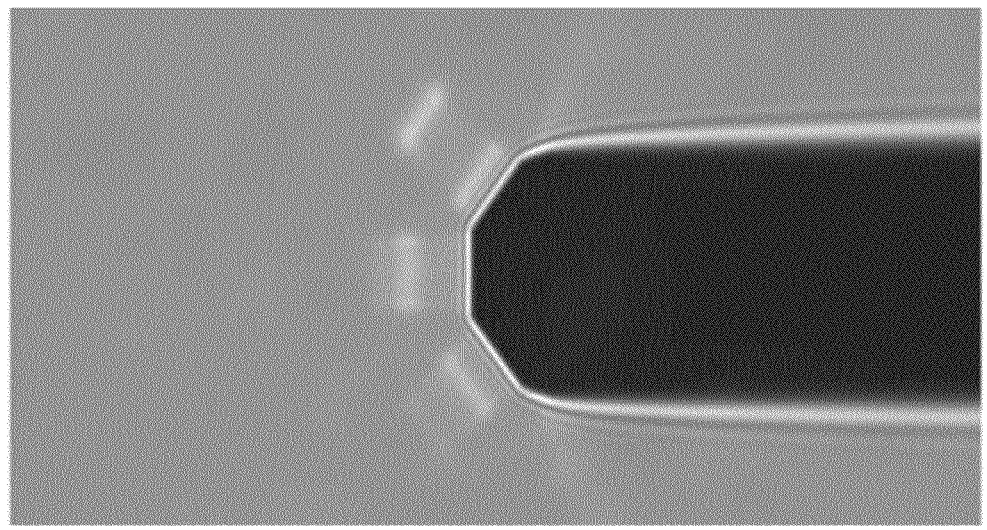
FIG. 4 is a partial side elevation view illustrating a calibration wafer as imaged by a shadow/edge profiler system.
Figure 5:
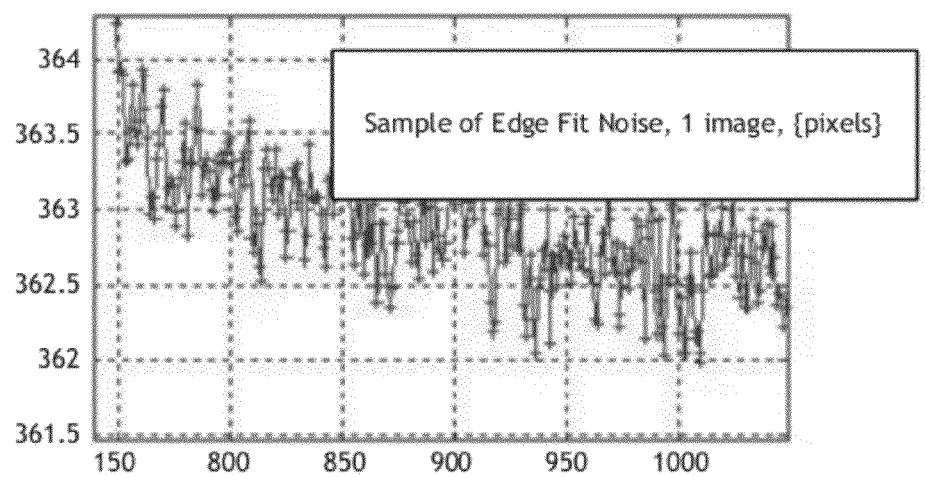
FIG. 5 is a data plot showing edge location measured by the shadow/edge profiler system along the top of the image of the calibration wafer as illustrated in FIG. 4.
Figure 6:
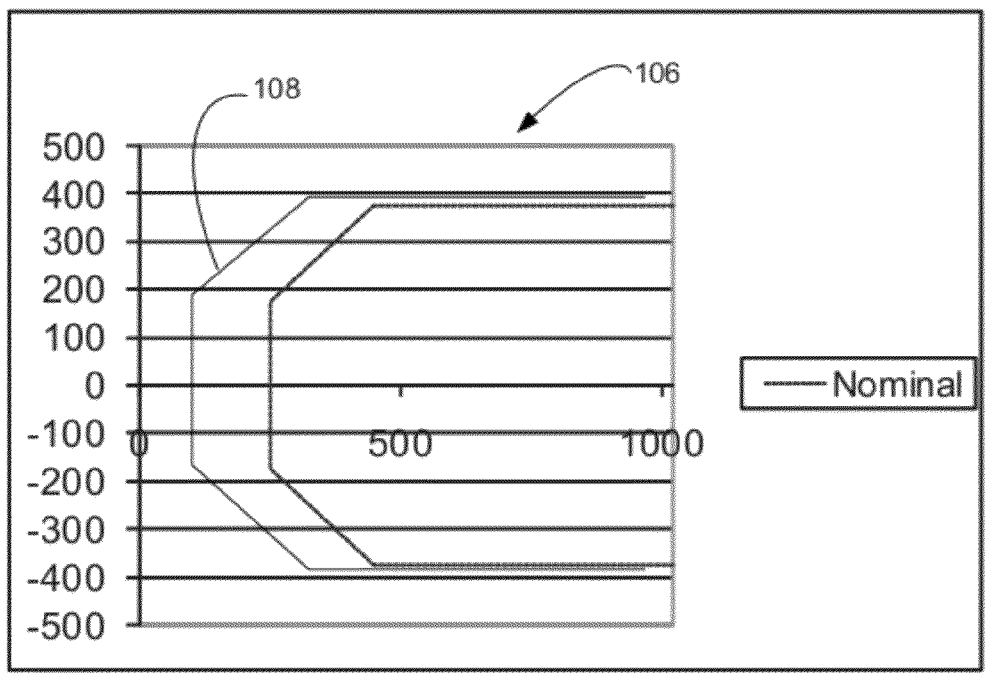
FIG. 6 is a partial side elevation view of the calibration wafer illustrated in FIG. 2, where the edge of the wafer is shown shifted from a nominal position with respect to the coordinate system.
Figure 7:
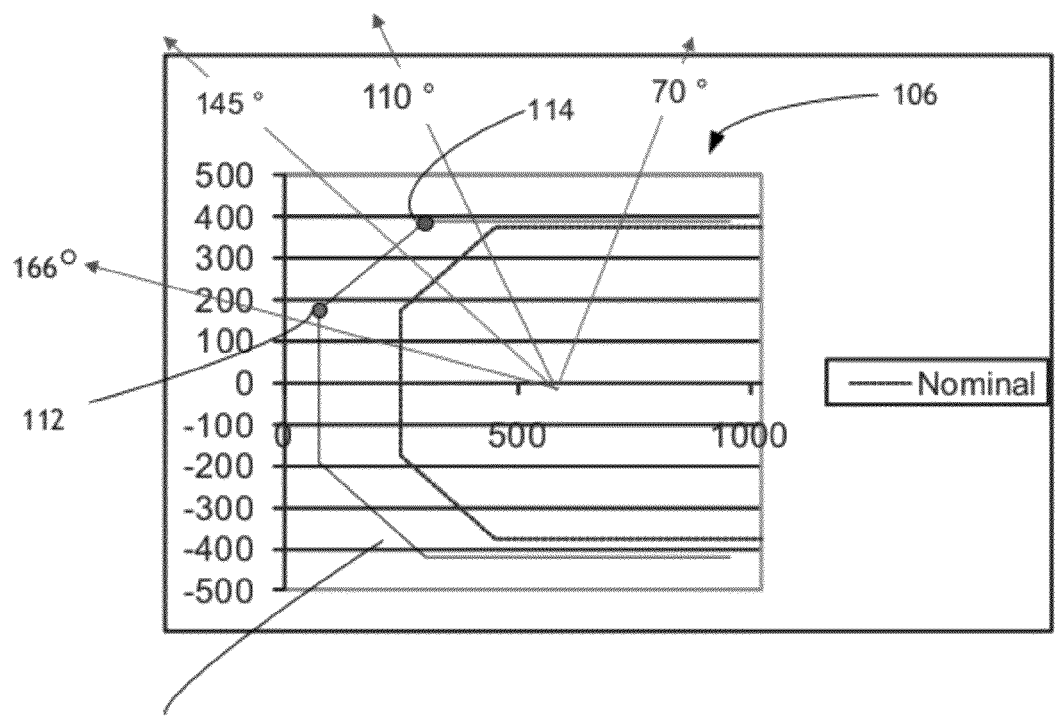
FIG. 7 is another partial side elevation view of the calibration wafer illustrated in FIG. 2, where the edge of the wafer is shown shifted from a nominal position with respect to the coordinate system, and the angles of first and second points on the edge of the calibration wafer are measured relative to a designed center of rotation.
Figure 8:
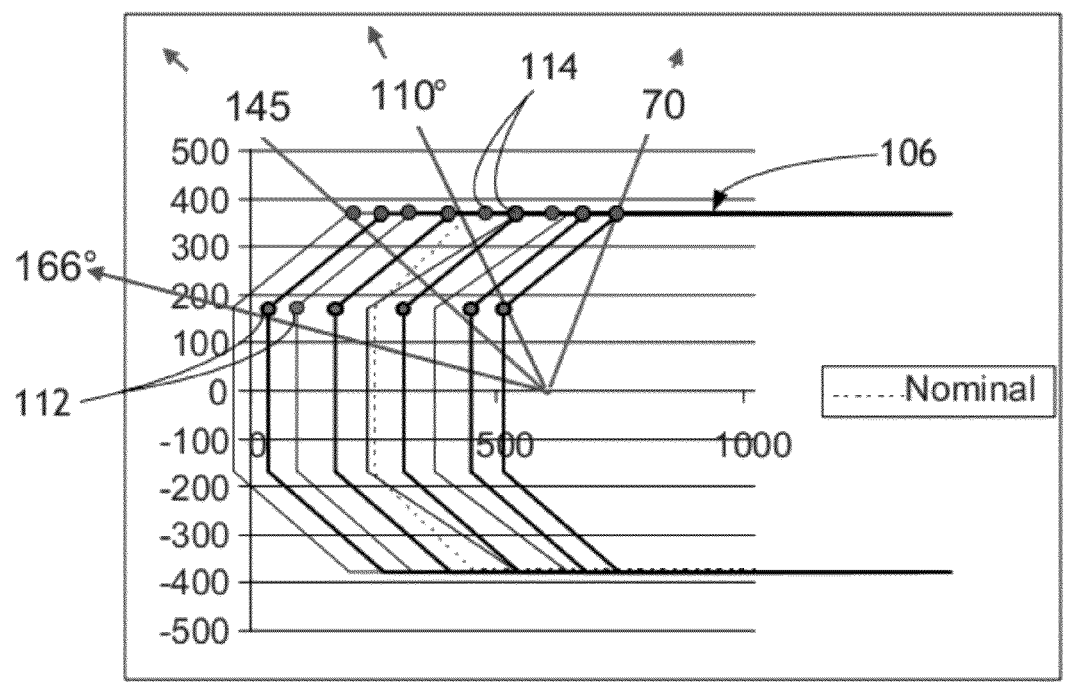
FIG. 8 is a still further side elevation view of the calibration wafer illustrated in FIG. 2, where the edge of the wafer is shown shifted into a number of different positions from a nominal position with respect to the coordinate system, and multiple angles for the first and second points on the edge of the calibration wafer are measured relative to the designed center of rotation.

Referring to FIGS. 3 through 5, in some embodiments, the facets of the discontinuous edge 108 of the calibration wafer 106 are designed to have grinding marks that alternate in angle. These alternating grinding marks may allow for easy location of the edge breaks in images taken by the edge imaging system 102. In other embodiments, grinding marks are not utilized. An edge break may indicate a first coordinate reference. Additionally, the length of each facet may be large enough to allow for easy detection by the shadow/edge profiler system 104 (more than 9 pixels in one embodiment), allowing multiple points to fit. In embodiments, this may allow for less than one-μm root mean square (RMS) location error. For example, the shadow/edge profiler system 104 may fit line segments, as illustrated in FIG. 4, and find an intersection. In one specific embodiment, single image RMS edge location may be 0.2 pixels (0.5 μm). Then, with a length of nominally 100 pixels, the intersection error may be 0.12 pixels RMS (or less than 0.3 μm) from a single image. It will be appreciated that when the edge imaging system 102 scan generates edge to closest pixel data, the granularity of the measurements may be limited by scan steps (up to one-μm in a specific embodiment) and intersection chips.

Figure 2:
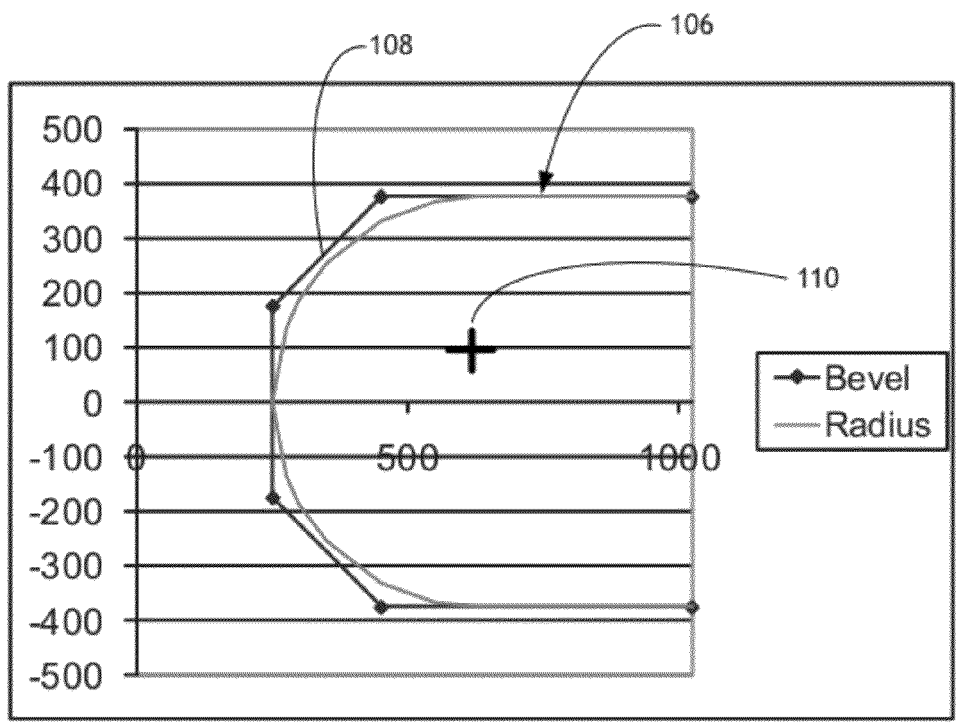
FIG. 2 is a partial side elevation view illustrating a calibration wafer profile superimposed on a coordinate system.

Referring now to FIG. 2, the facets of the discontinuous edge 108 of the calibration wafer 106 may be ground tangent to one or more points along the circumference of a semi-circle having a radius according to a coordinate system superimposed against a profile of the calibration wafer 106. In other embodiments, the facets may be ground to a radius, such as to avoid defocus from the laser scanning image. The center of the semi-circle may be referred to as the designed center of rotation 110. In the coordinate system illustrated in FIG. 2, the designed center of rotation 110 is located at coordinates (625,0) μm.

Figure 9:
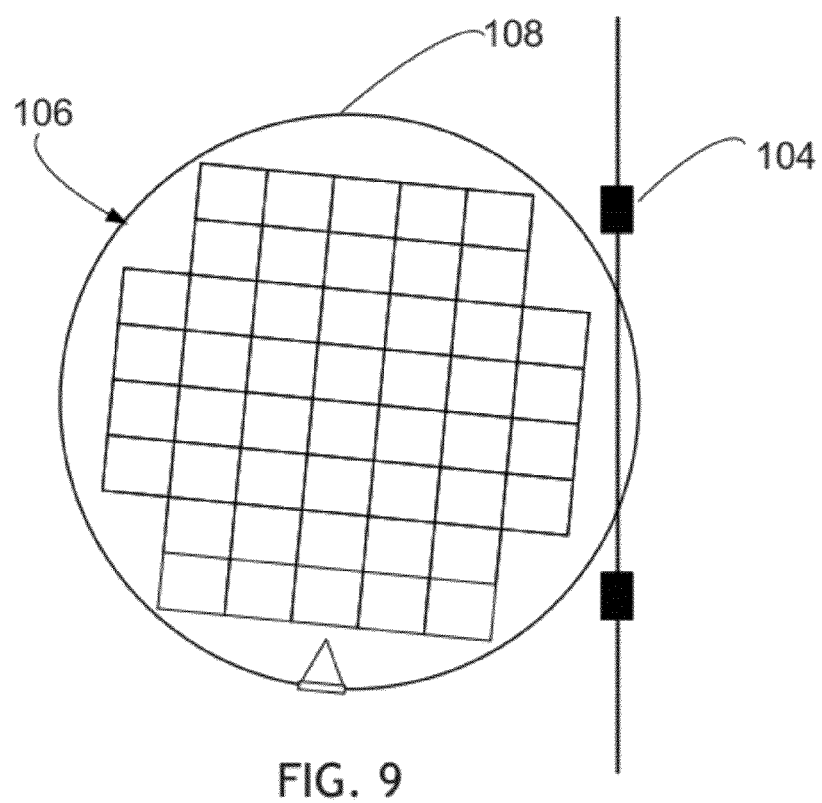
FIG. 9 is a top plan view illustrating a calibration wafer as rotated about an eccentric axis.
Figure 10:
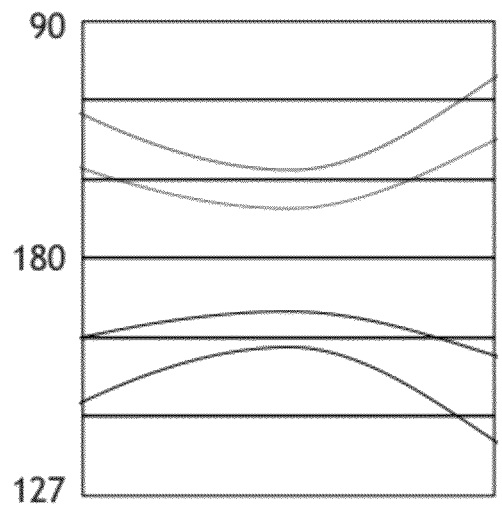
FIG. 10 is a side scan window illustrating the sinusoidal nature of the measurements taken in FIG. 8 and in other figures.
Figure 11:
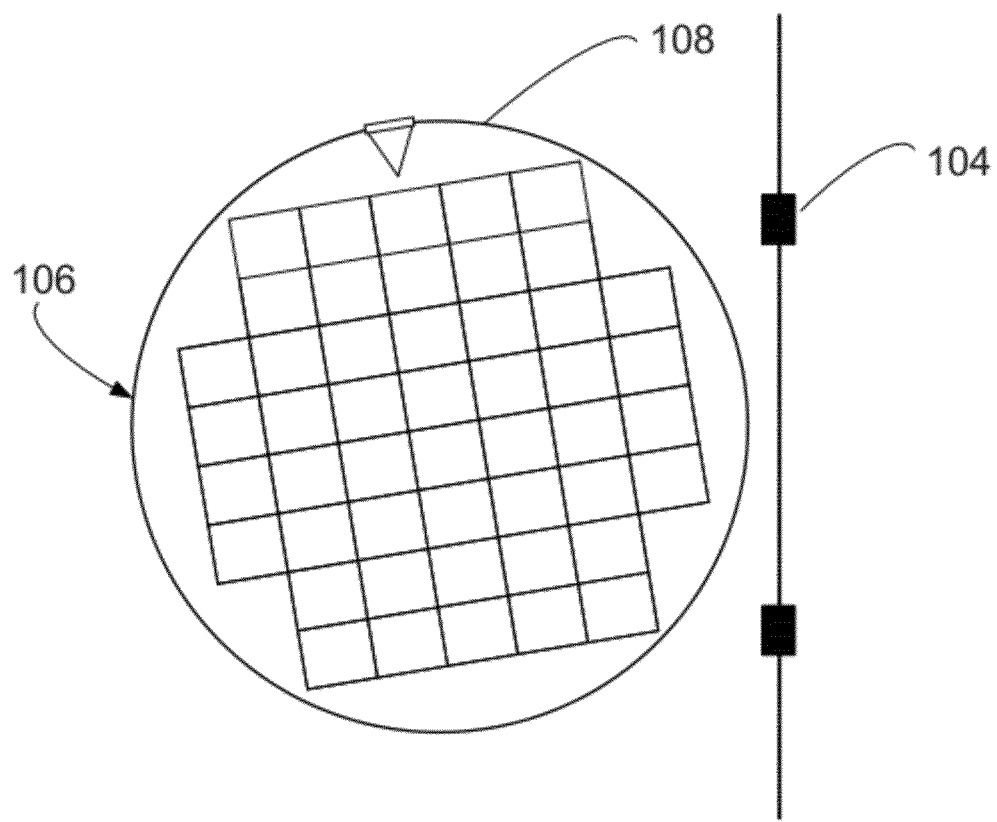
FIG. 11 is another top plan view of the calibration wafer as further rotated about its eccentric axis as illustrated in FIG. 9.
Figure 12:
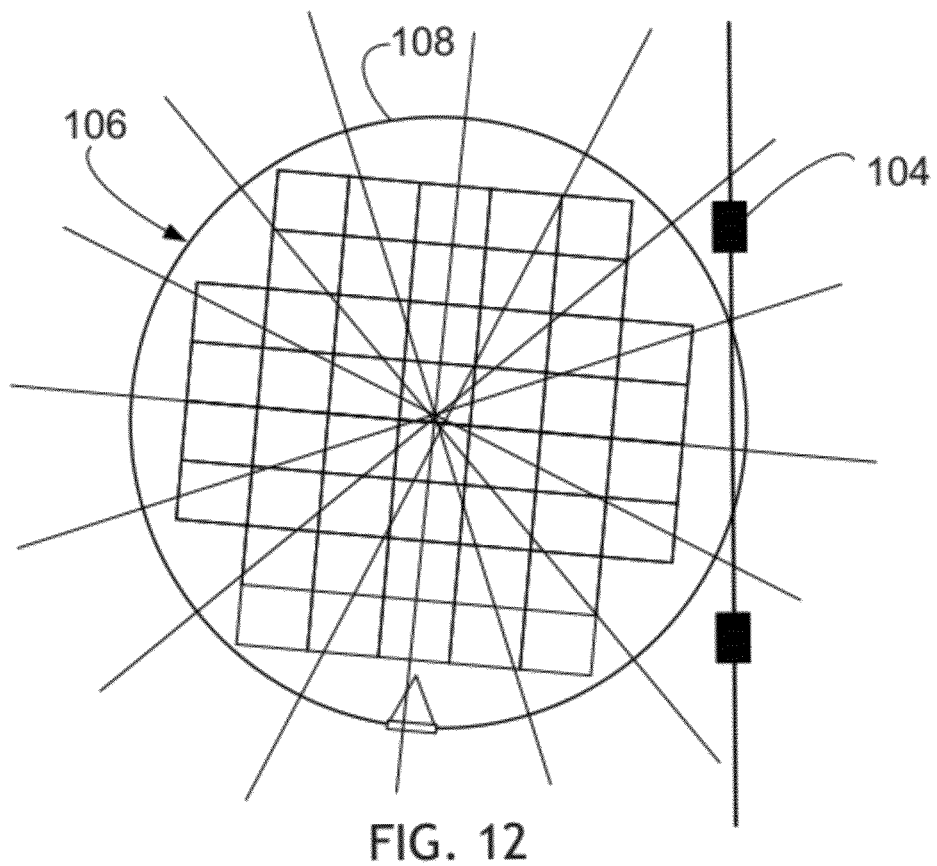
FIG. 12 is a still further top plan view of the calibration wafer as rotated about its eccentric axis as illustrated in FIG. 9, where the calibration wafer has been divided into even intervals.
Figure 13:
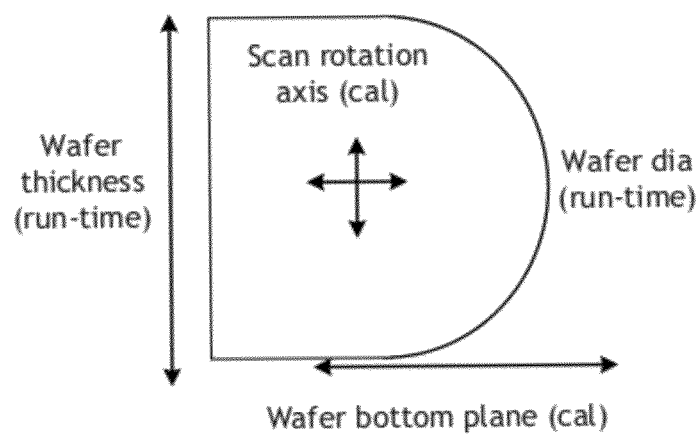
FIG. 13 is a partial side elevation view illustrating a wafer with calibrations and run-time corrections superimposed thereupon.
Figure 14:
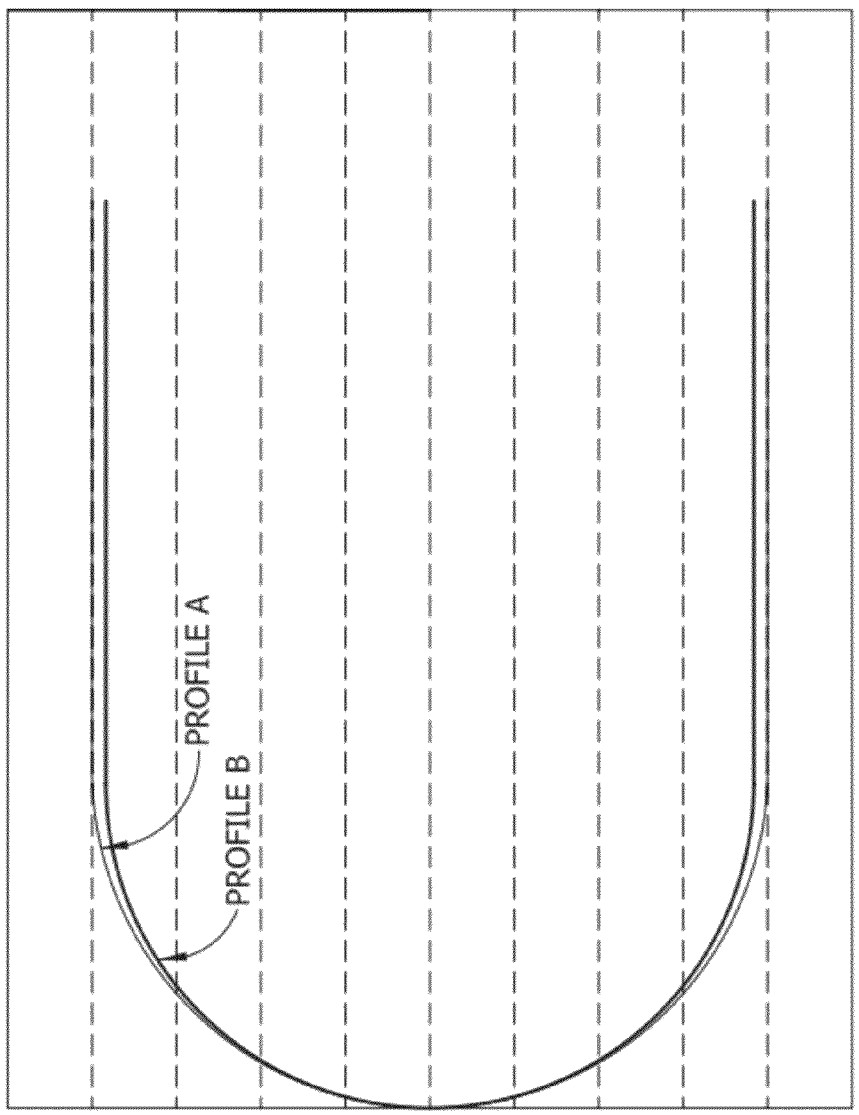
FIG. 14 is a partial side elevation view illustrating a coordinate system with computed wafer profiles superimposed thereupon.

Referring now to FIGS. 6 through 12, the calibration wafer 106 is rotated about an apparent eccentric axis (i.e., with respect to the shadow/edge profiler system 104), such that the discontinuous edge 108 of the calibration wafer 106 shifts in a smooth sinusoid (as seen in FIG. 10) with respect to the shadow/edge profiler system 104 (as seen in FIGS. 9, 11, and 12). In some embodiments, the apparent eccentric axis of rotation of the calibration wafer 106 is obtained by utilizing an offset wafer center axis, while in other embodiments the shadow/edge profiler system 104 (and/or the edge imaging system 102) may be translated back and forth with respect to the calibration wafer 106. By measuring the angles from the designed center of rotation 110 to a first point 112 (i.e., a second coordinate reference) and a second point 114 (i.e., another coordinate reference), while the calibration wafer 106 is rotated, the features of the calibration wafer 106 may more accurately be determined. Being able to create an accurate vertical coordinate fusion for the calibration wafer 106 utilizing multiple data points with the non-destructive calibration techniques described, features of the calibration wafer 106 may be located with micrometer-level accuracy. For example, with reference to the previous description, the first coordinate reference at the edge break determined by the edge imaging system 102 may be correlated/mapped to the first point 112/second coordinate reference determined utilizing the shadow/edge profiler system 104.

Referring now to FIGS. 13 through 17, a method 1700 for generating an image and a profile of a semiconductor wafer, where the image includes a first coordinate reference and the profile includes a second coordinate reference, and where the method includes mapping the first coordinate reference to the second coordinate reference. First, a semiconductor wafer having a discontinuous edge is rotatably supported, 1710. Then, an image of the semiconductor wafer is generated by scanning a first region on an edge of the semiconductor wafer, a second region on a first side of the semiconductor wafer proximal to the edge of the semiconductor wafer, and a third region on a second side of the semiconductor wafer proximal to the edge of the semiconductor wafer, where the image includes a first coordinate reference, 1720. Next, a profile of the semiconductor wafer is generated by projecting at least nominally collimated light in a direction at least substantially parallel to the first side of the semiconductor wafer and the second side of the semiconductor wafer, the at least nominally collimated light projected past the edge of the semiconductor wafer, where the profile includes a second coordinate reference, 1730. Coordinate transformations are determined by locating at least one structural feature of the discontinuous edge of the semiconductor wafer which is located on both the image and the profile, 1740. Finally, a first coordinate reference is mapped to the second coordinate reference utilizing the location of the at least one structural feature of the discontinuous edge of the semiconductor wafer to determine locations of features of wafers under inspection, 1750.

In embodiments, the calibration wafer 106 may be scanned in order to calibrate the edge imaging system 102 to the shadow/edge profiler system 104. First, scan optics axis of rotation (Y-axis) may be utilized for a known standard wafer. Then, reference edge determination on edge profile and correlation to optics image may be performed. Finally, an ideal edge shape from the scan may be aligned to the wafer bottom plane. Then, at run-time, a scan optics head working distance correction (X-axis) may be made based upon an apex extreme location from the edge profile. This step may be performed on a per-wafer basis. Next, wafer thickness correction on a per-wafer basis (Z-height from top) may be performed. Finally, an edge profile trace alignment to scan optics sweep may be performed.

Figure 15:
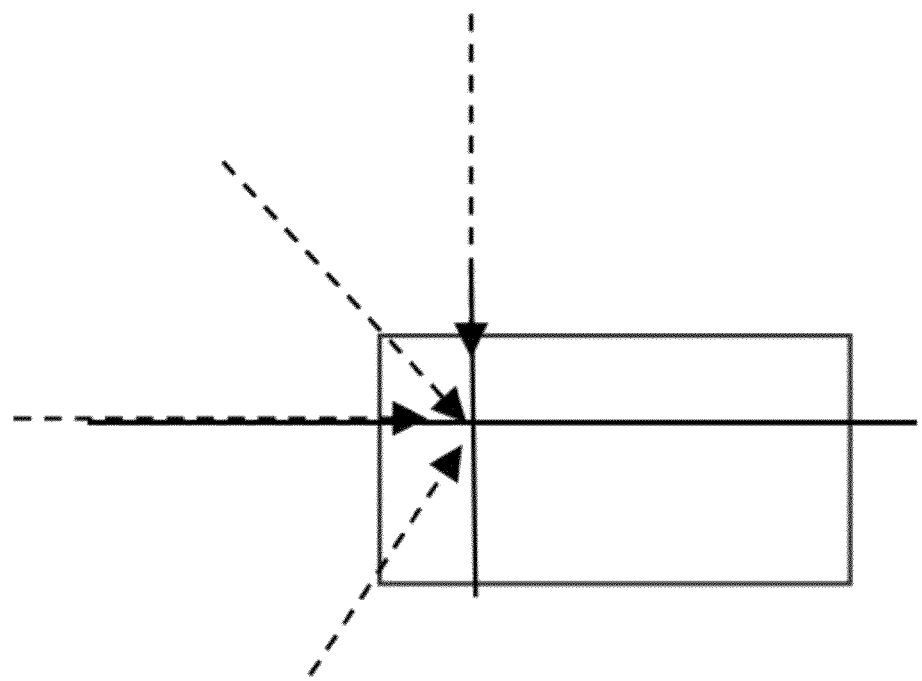
FIG. 15 is a partial side elevation view illustrating a square edged calibration wafer, where a rotation center point is superimposed upon the calibration wafer.
Figure 16:
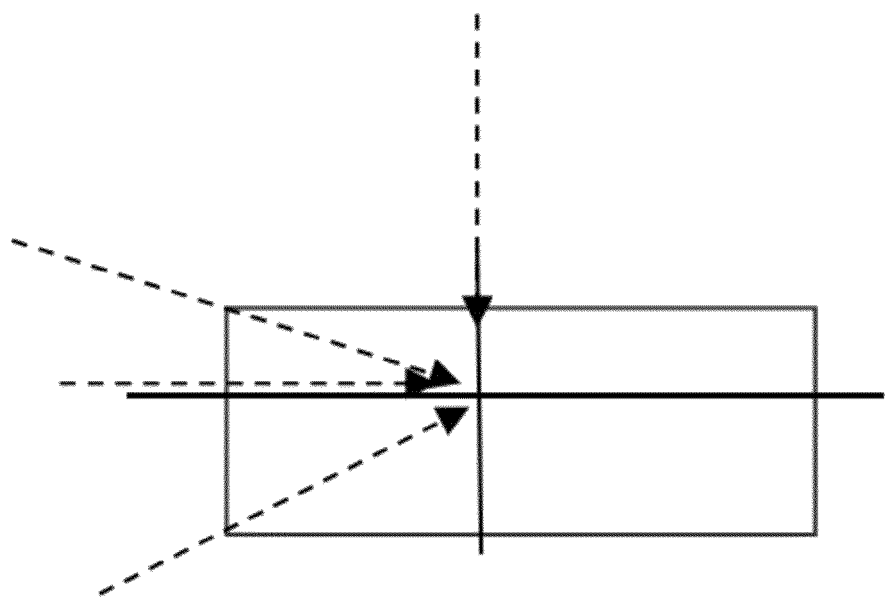
FIG. 16 is another partial side elevation view of the square edged calibration wafer illustrated in FIG. 15, where another rotation center point is superimposed upon the calibration wafer.
Figure 17:
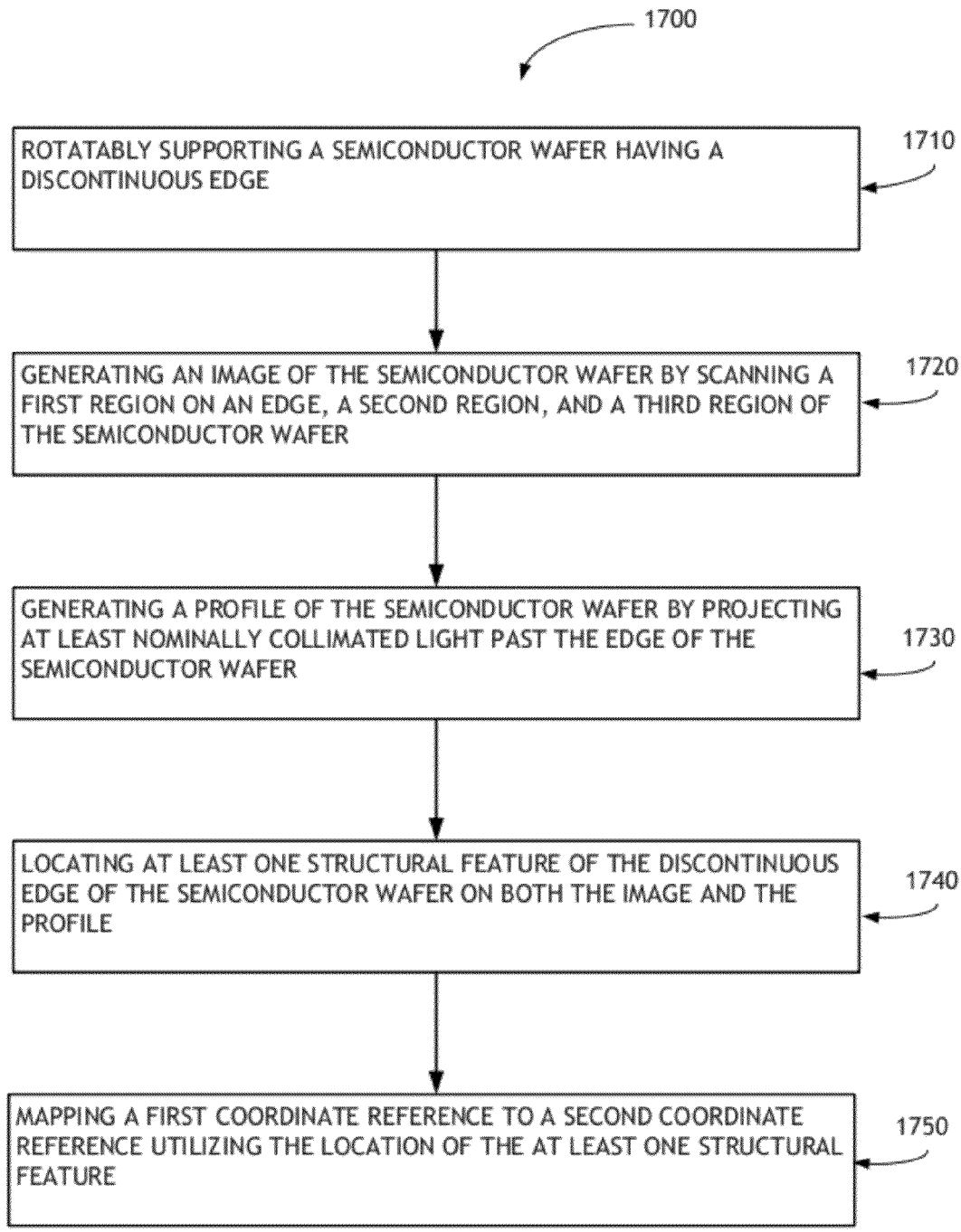
FIG. 17 is a flow diagram illustrating a method for generating an image and a profile of a semiconductor wafer, where the image includes a first coordinate reference and the profile includes a second coordinate reference, and where the method includes mapping the first coordinate reference to the second coordinate reference.
Figure 18:
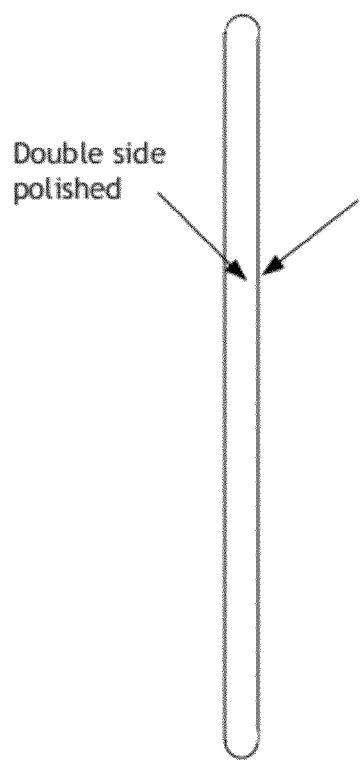
FIG. 18 is a side view illustrating an available starting material for a calibration wafer, where the starting material is a semi-standard blank shiny wafer formed of silicon with a beveled edge.
Figure 19:
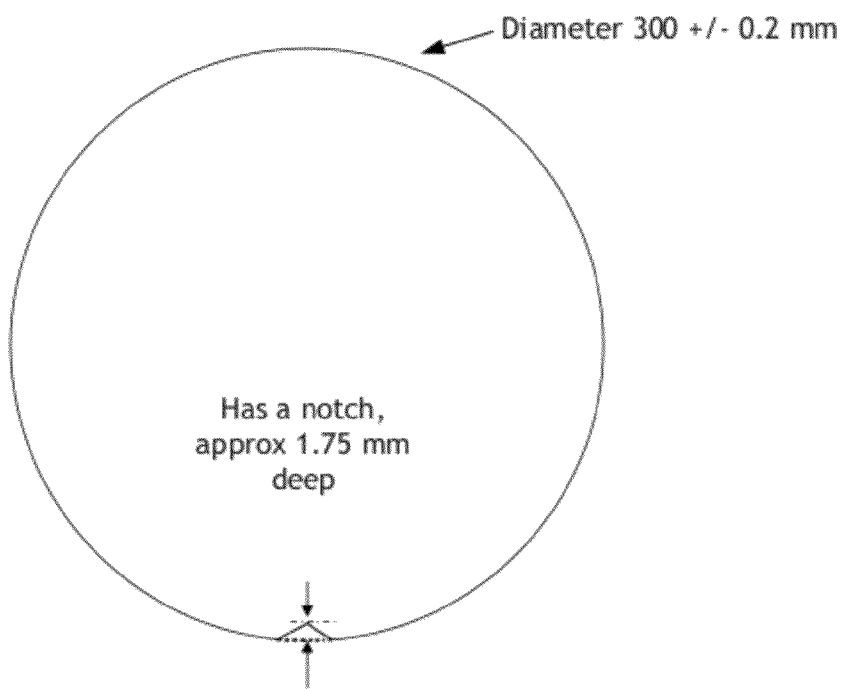
FIG. 19 is a top plan view of the available starting material for the calibration wafer illustrated in FIG. 18.
Figure 20:
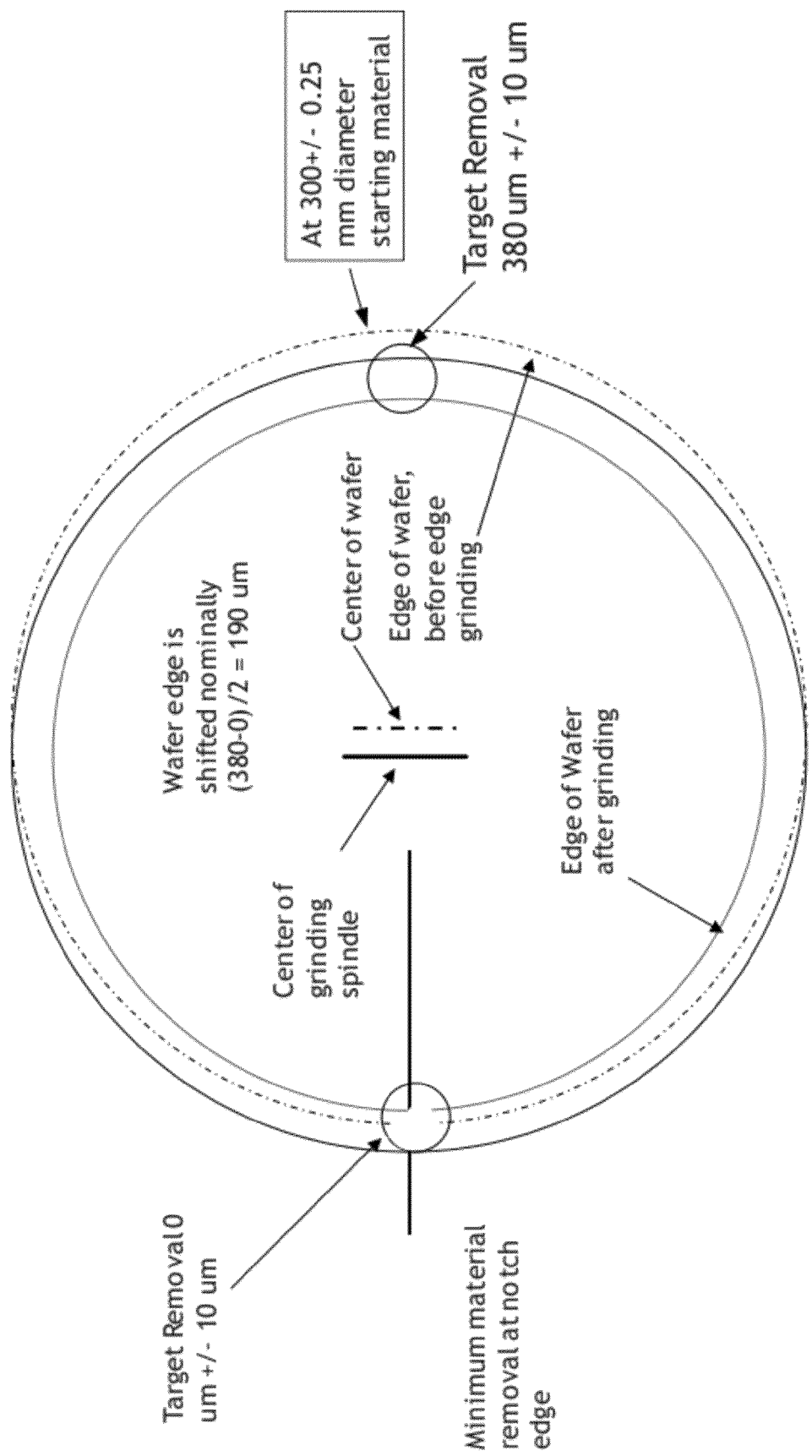
FIG. 20 is a top plan view of the calibration wafer illustrated in FIG. 18, where the calibration wafer undergoes a first step of grinding and finishing.
Figure 22:
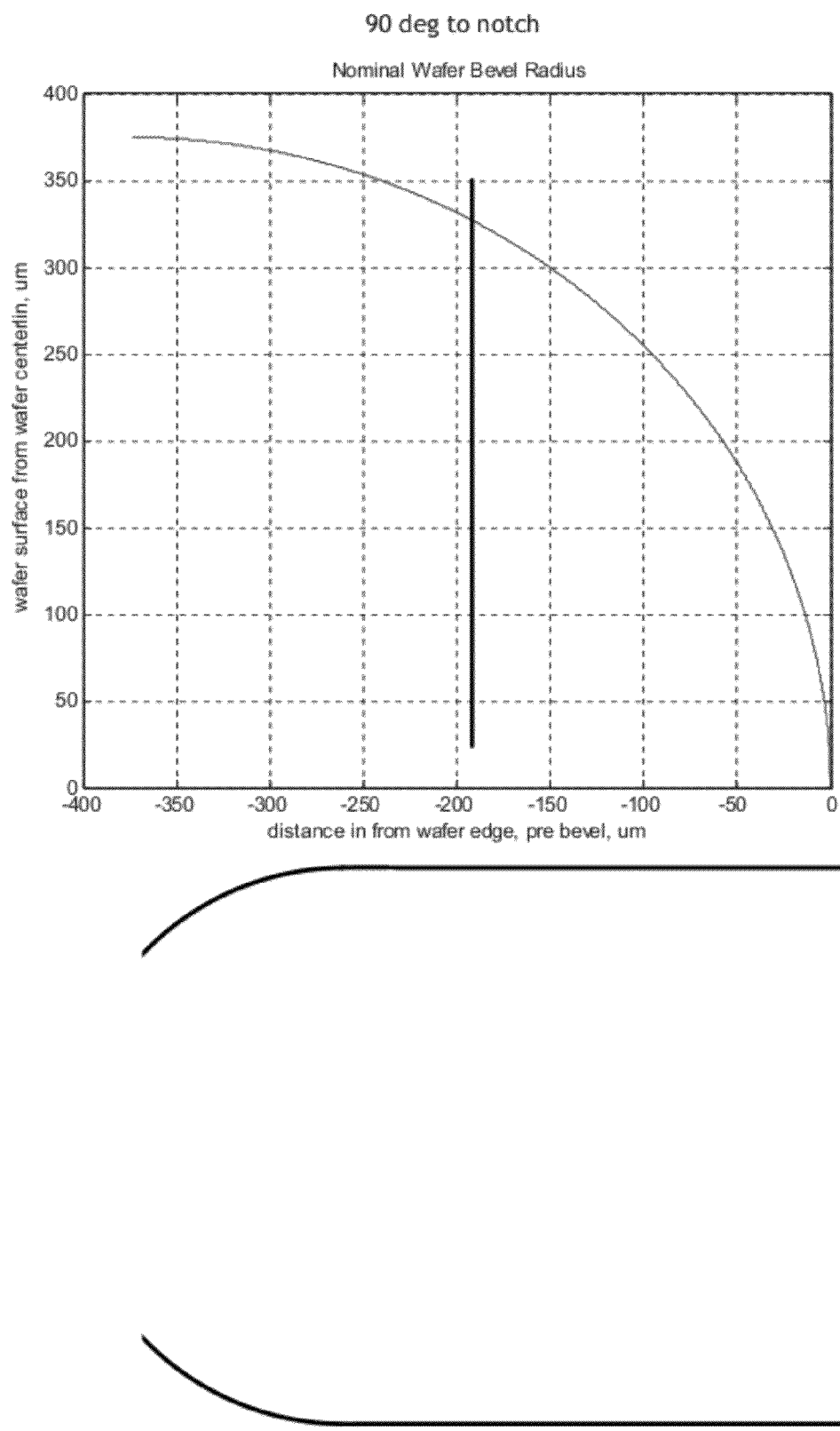
Figure 23:
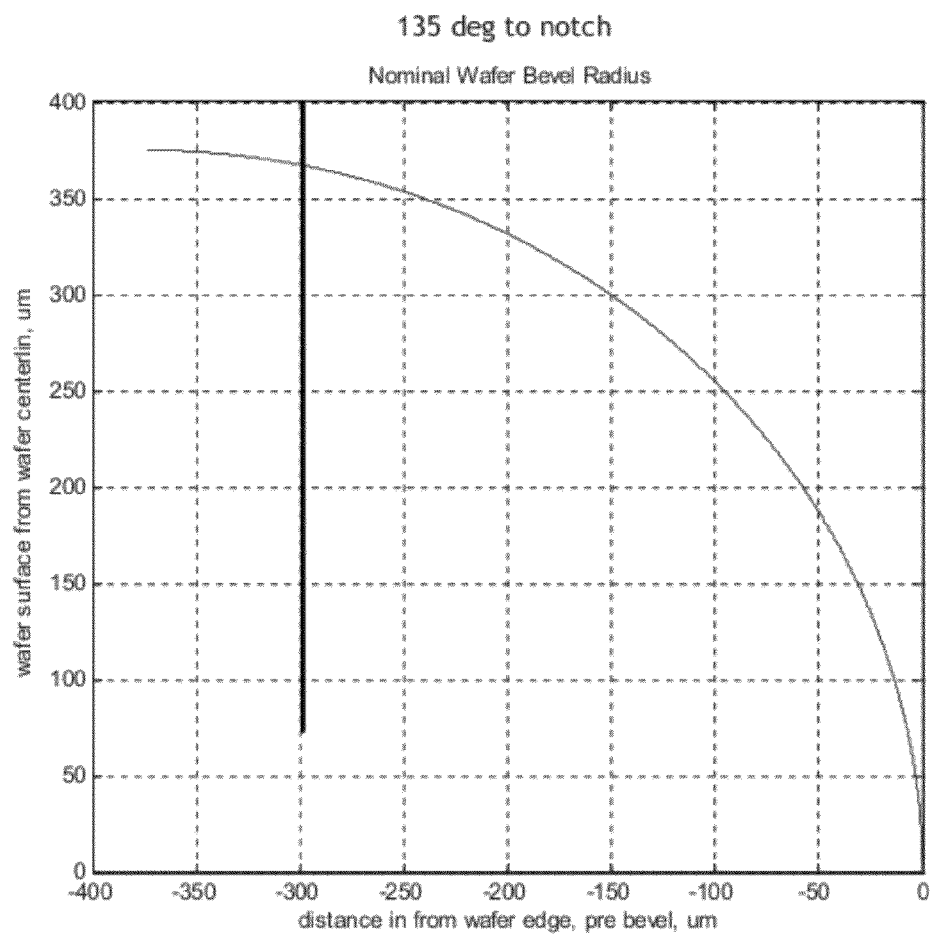
Figure 24:
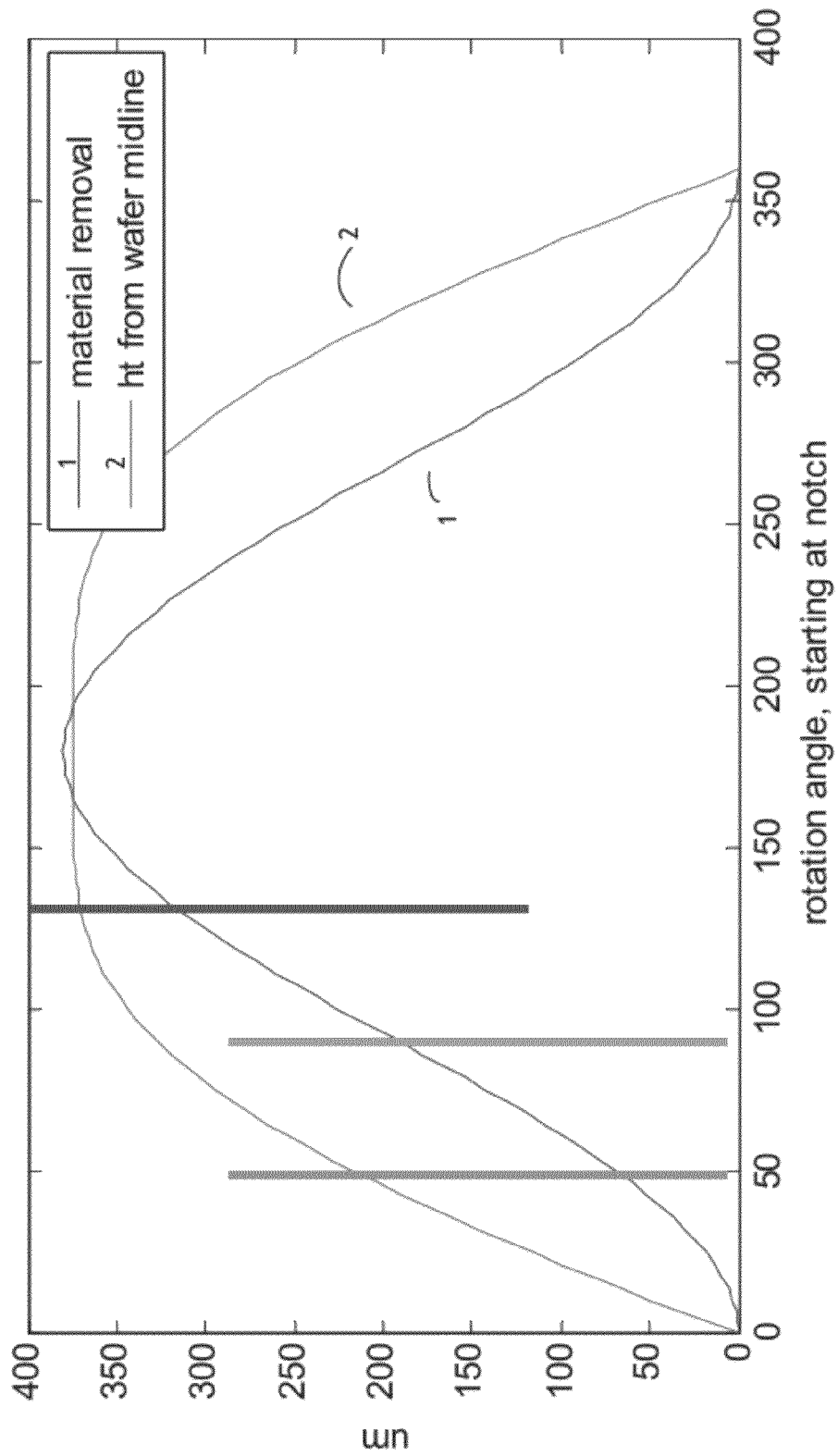
FIG. 24 illustrates a rotation angle starting at notch for the calibration wafer illustrated in FIG. 18.
Figure 26:
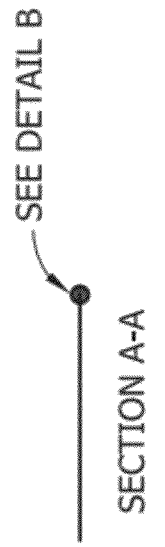
FIG. 26 is a partial side elevation view of the calibration wafer illustrated in FIG. 25.
Figure 25:
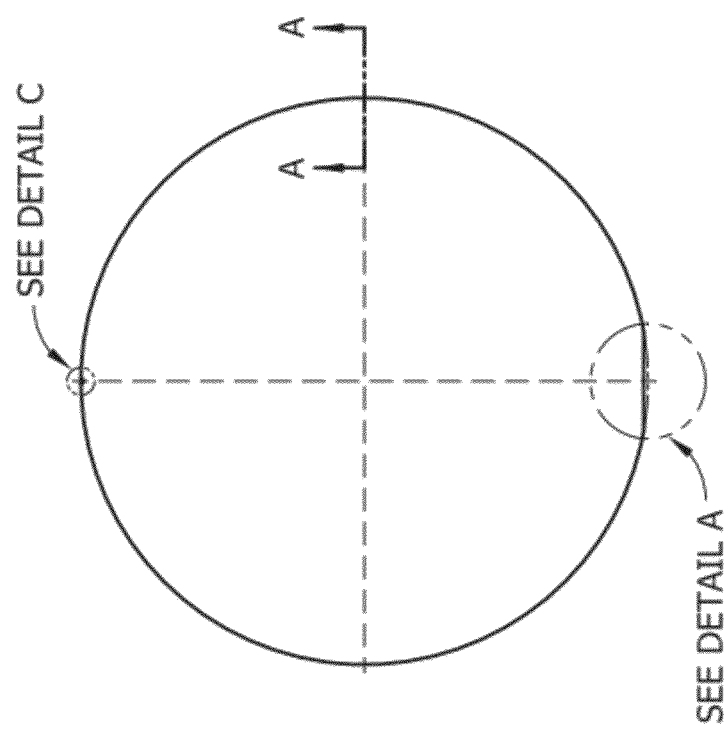
FIG. 25 is a top plan view illustrating another type of calibration wafer.
Figure 28:
FIG. 28 is another partial top plan view of the calibration wafer illustrated in FIG. 25.
Figure 27:
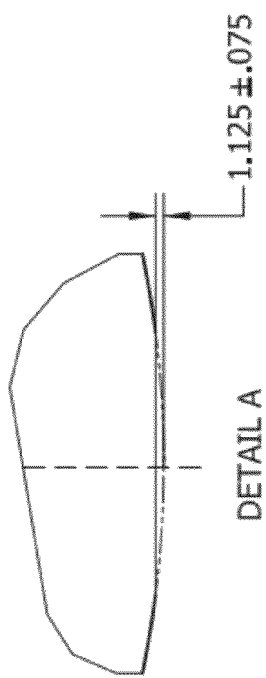
FIG. 27 is a partial top plan view of the calibration wafer illustrated in FIG. 25.
Figure 29:
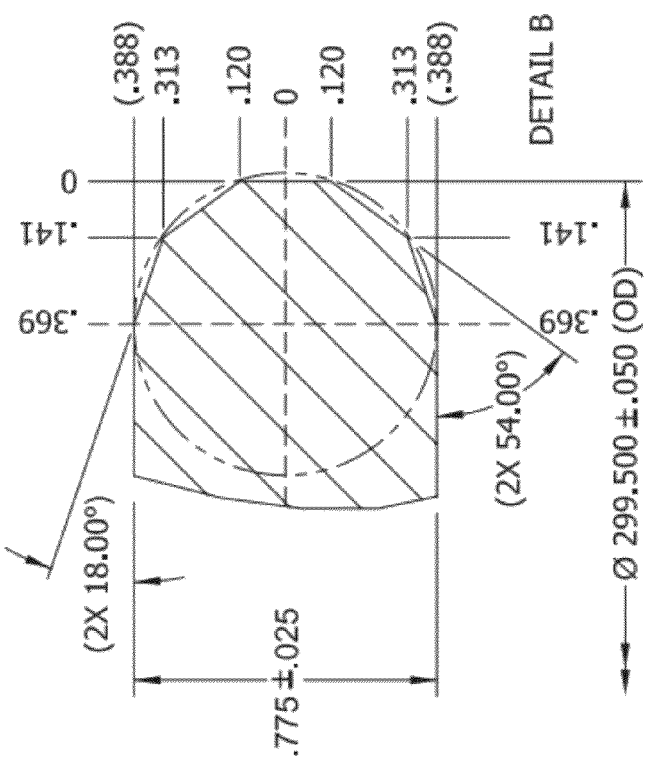
FIG. 29 is a partial cross-sectional side elevation view of the calibration wafer illustrated in FIG. 25.
Figure 30:
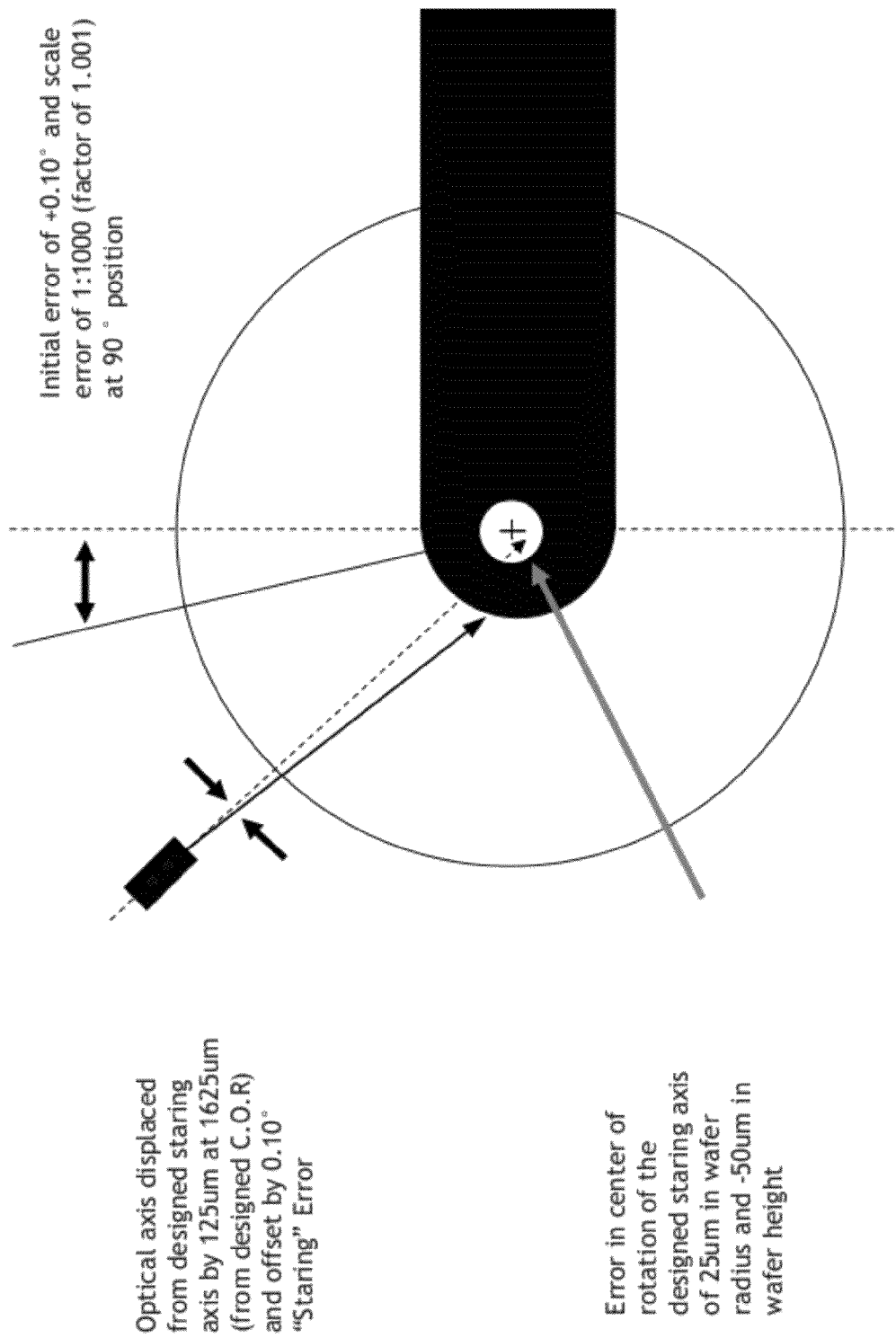
FIG. 30 is a top plan view illustrating a graphical calibration example.
Figure 31:
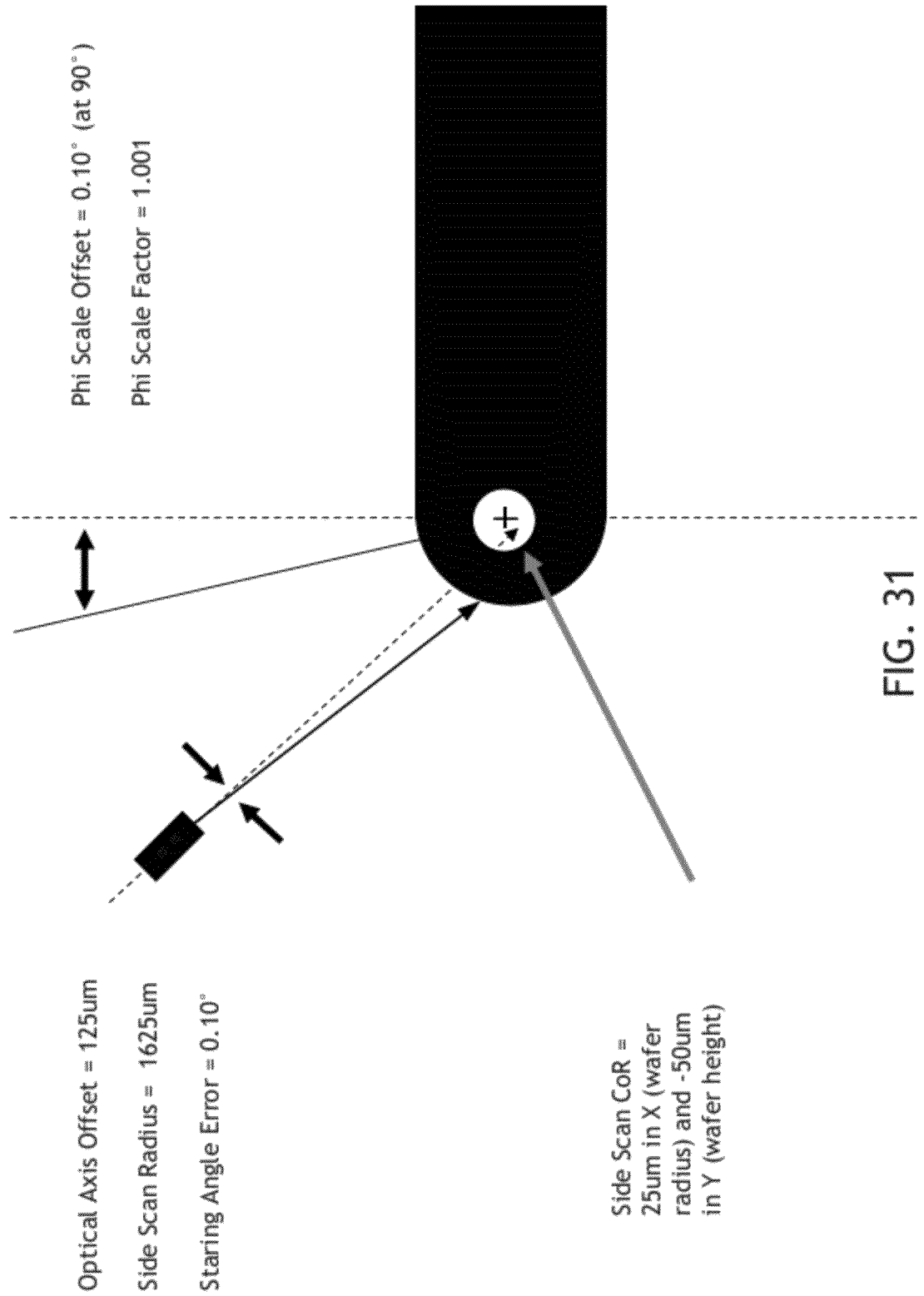
FIG. 31 is a top plan view illustrating back solving from an actual "Phi" to a measured.
Figure 32:
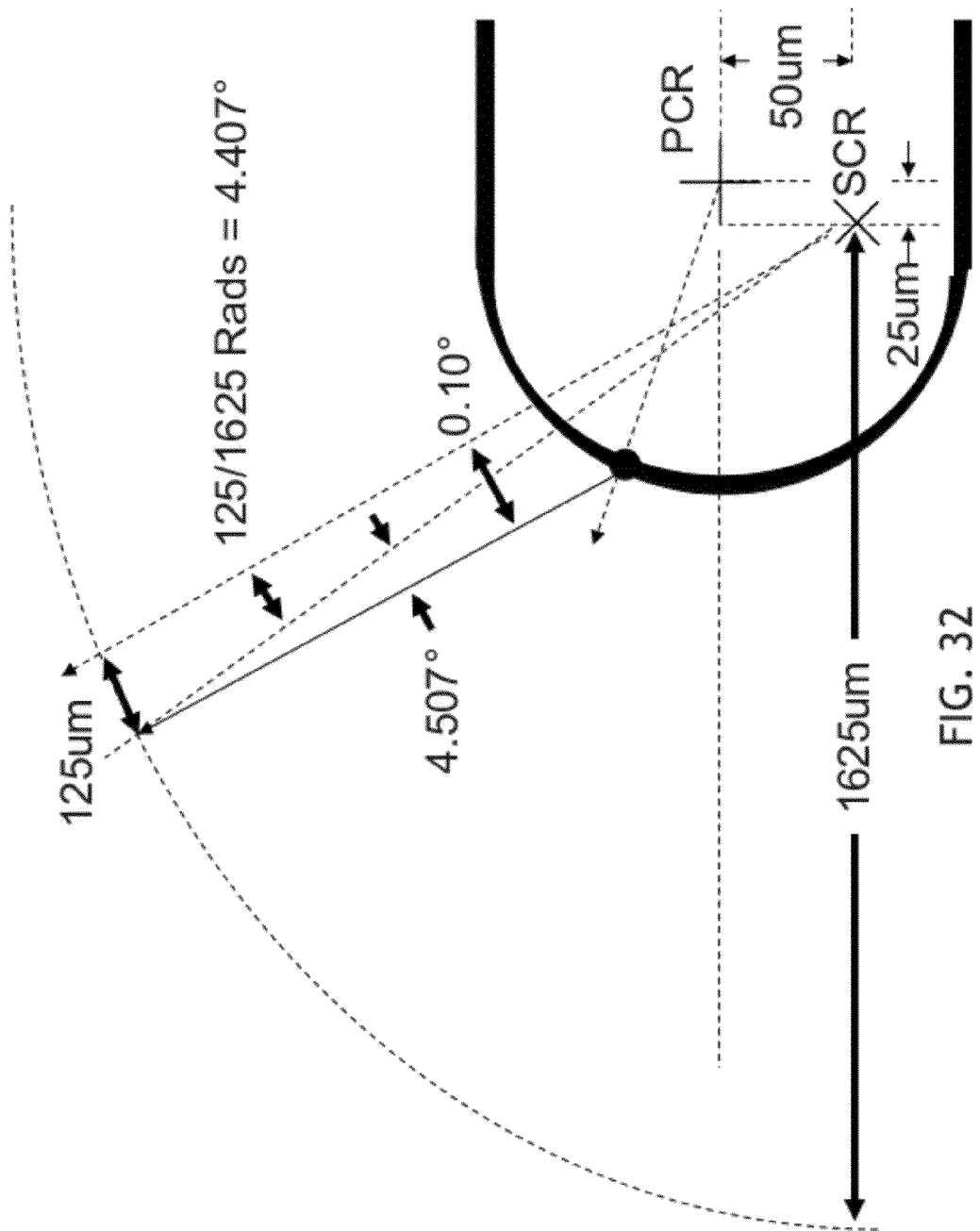
FIG. 32 is a partial side elevation view illustrating back solving from an actual "Phi" to a measured.
Figure 33:
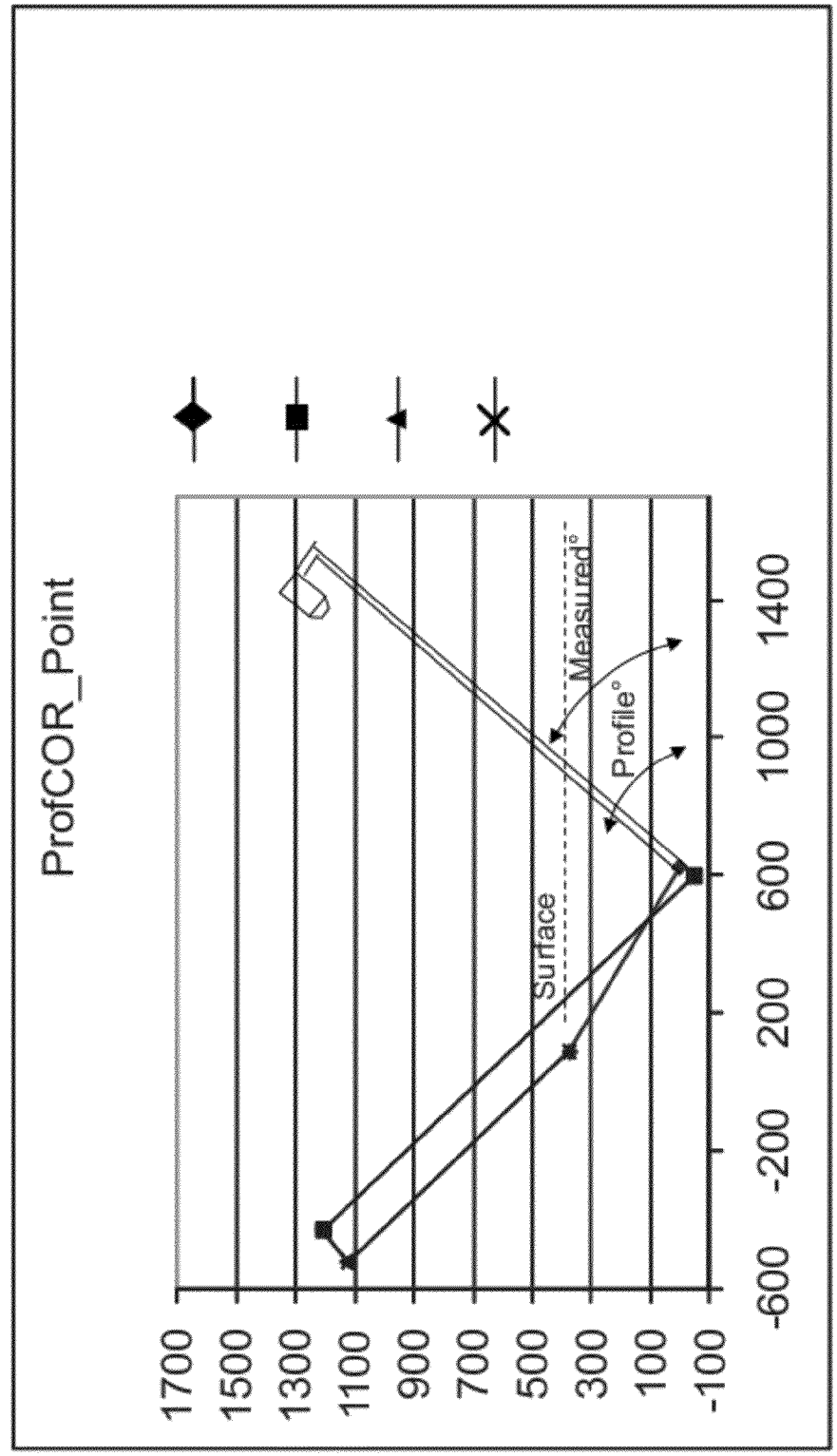
FIG. 33 is an example of an uncalibrated measurement error.
Figure 34:
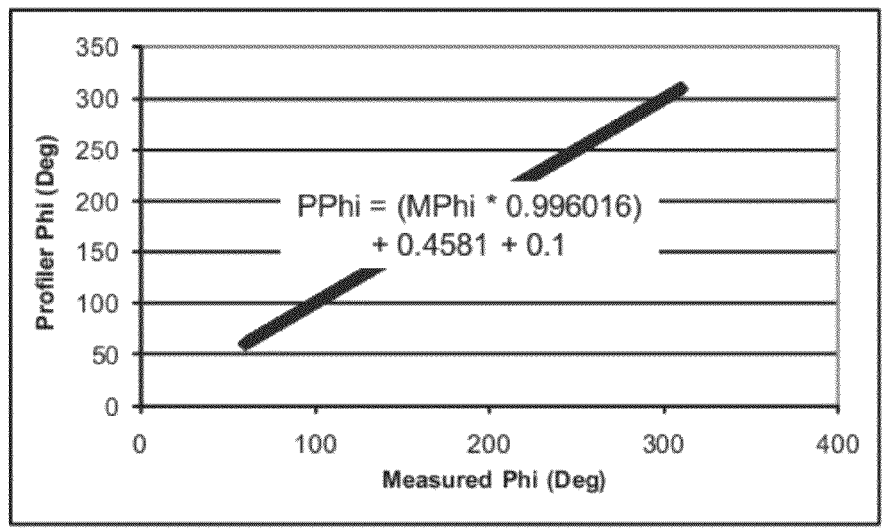
FIGS. 34 through 37 illustrate calibration output utilizing known model data to generate a derived solution.
Figure 35:
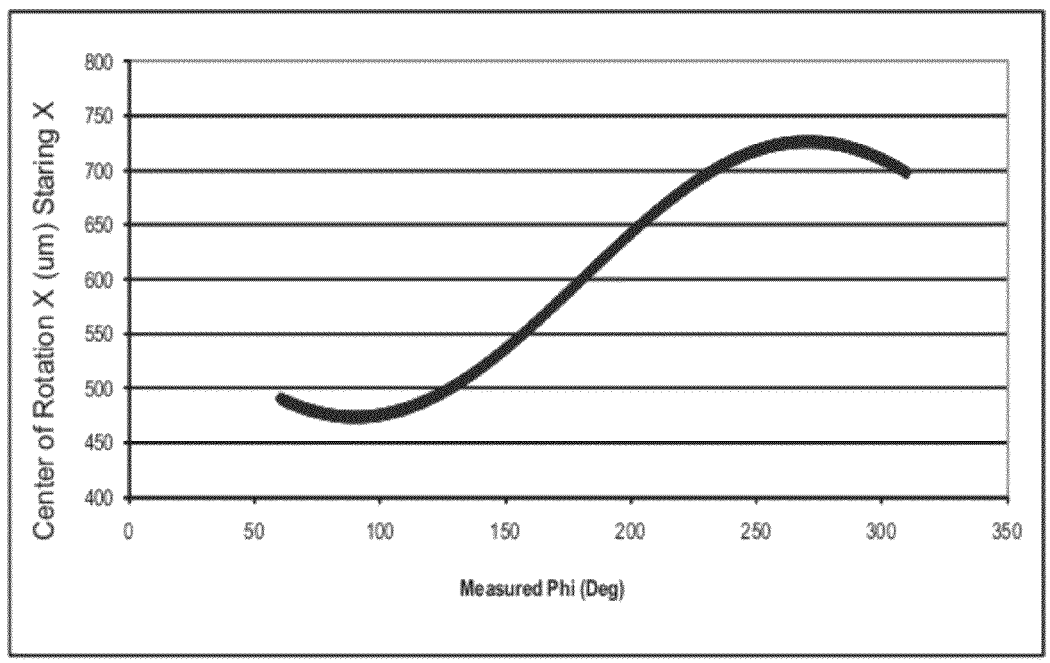
Figure 36:
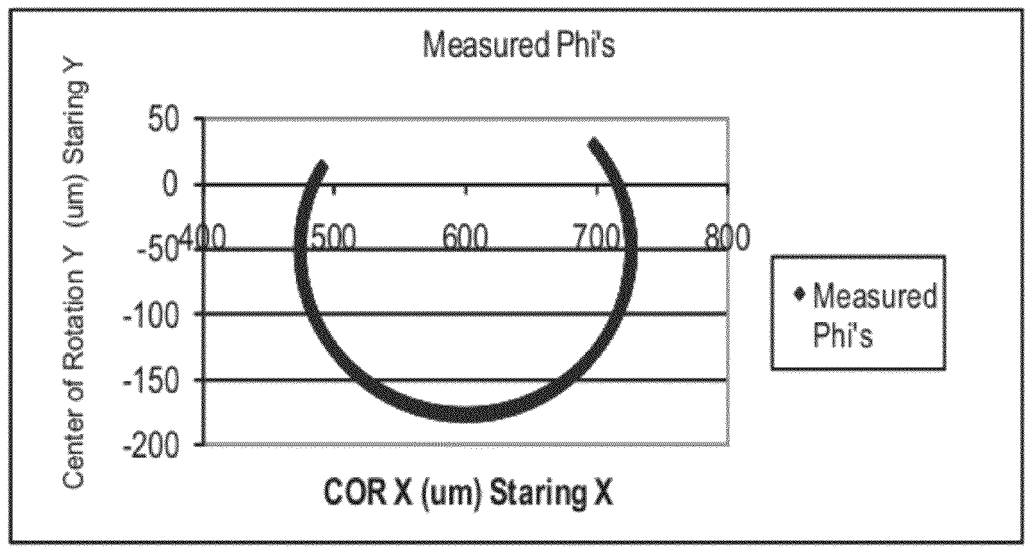
Figure 37:
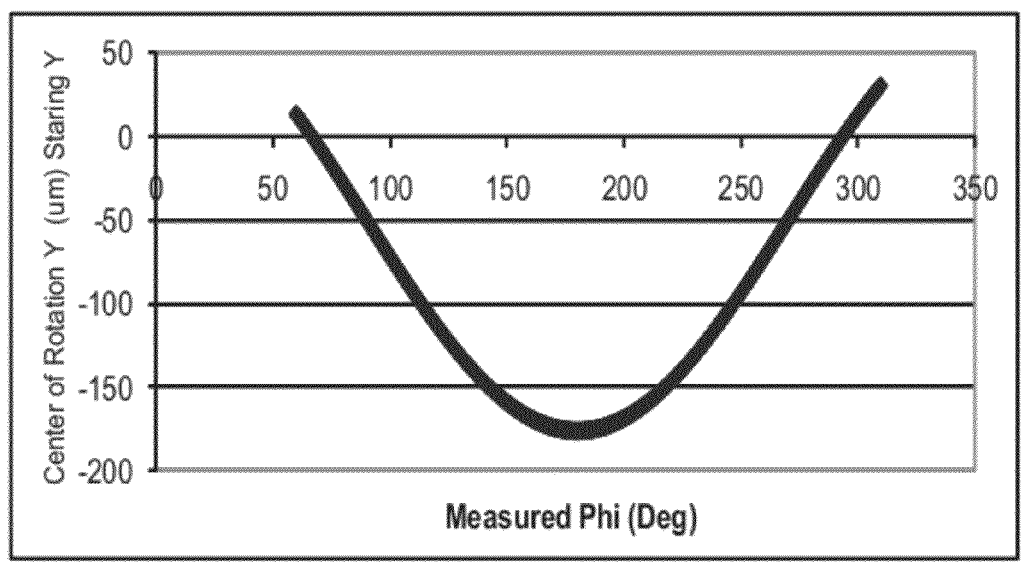
Figure 38:
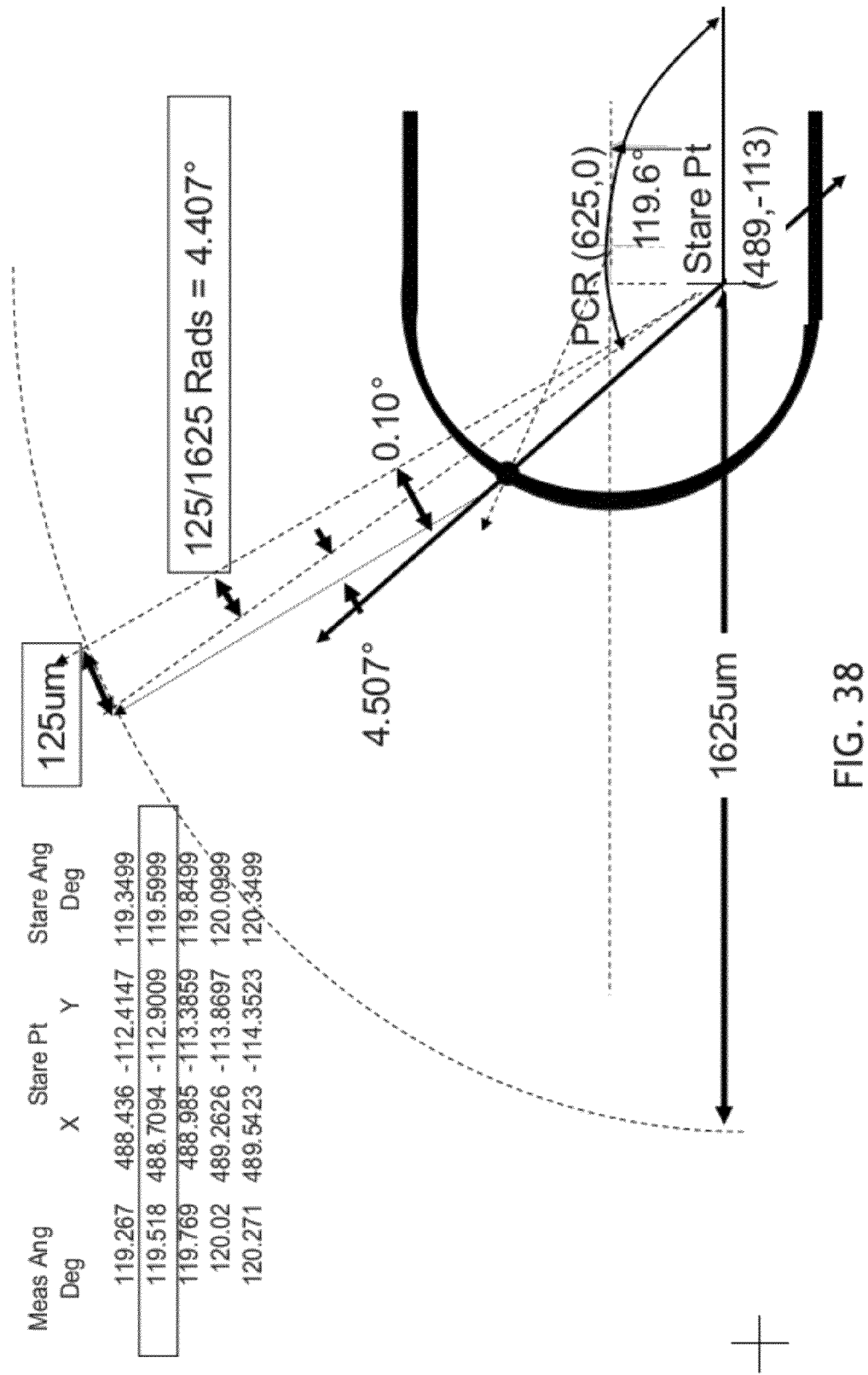
FIG. 38 is a graphical illustration of applying a calibration.
Figure 39:
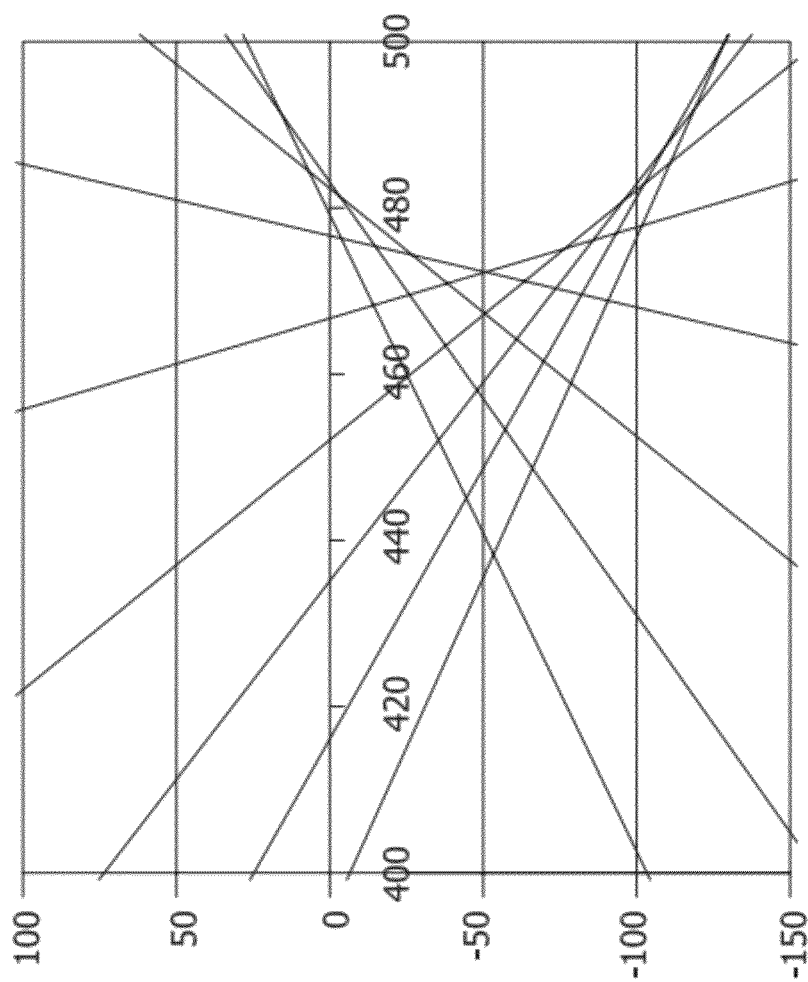
FIGS. 39 through 42 illustrate center of rotation/staring circle calculation techniques, where "local center of rotations" are solved for as the intersections of lines passing through neighboring points.
Figure 40:
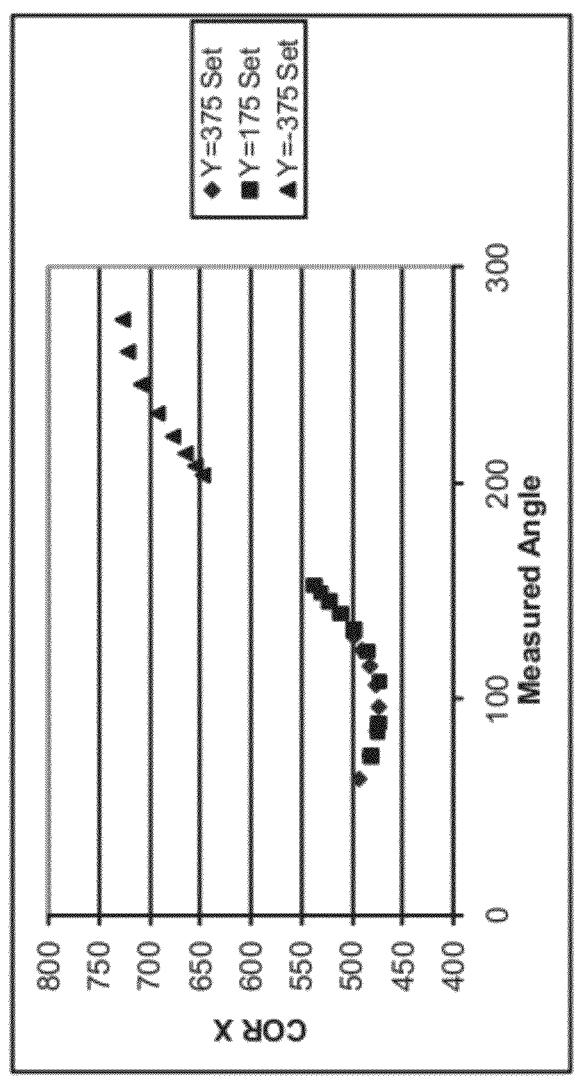
Figure 41:
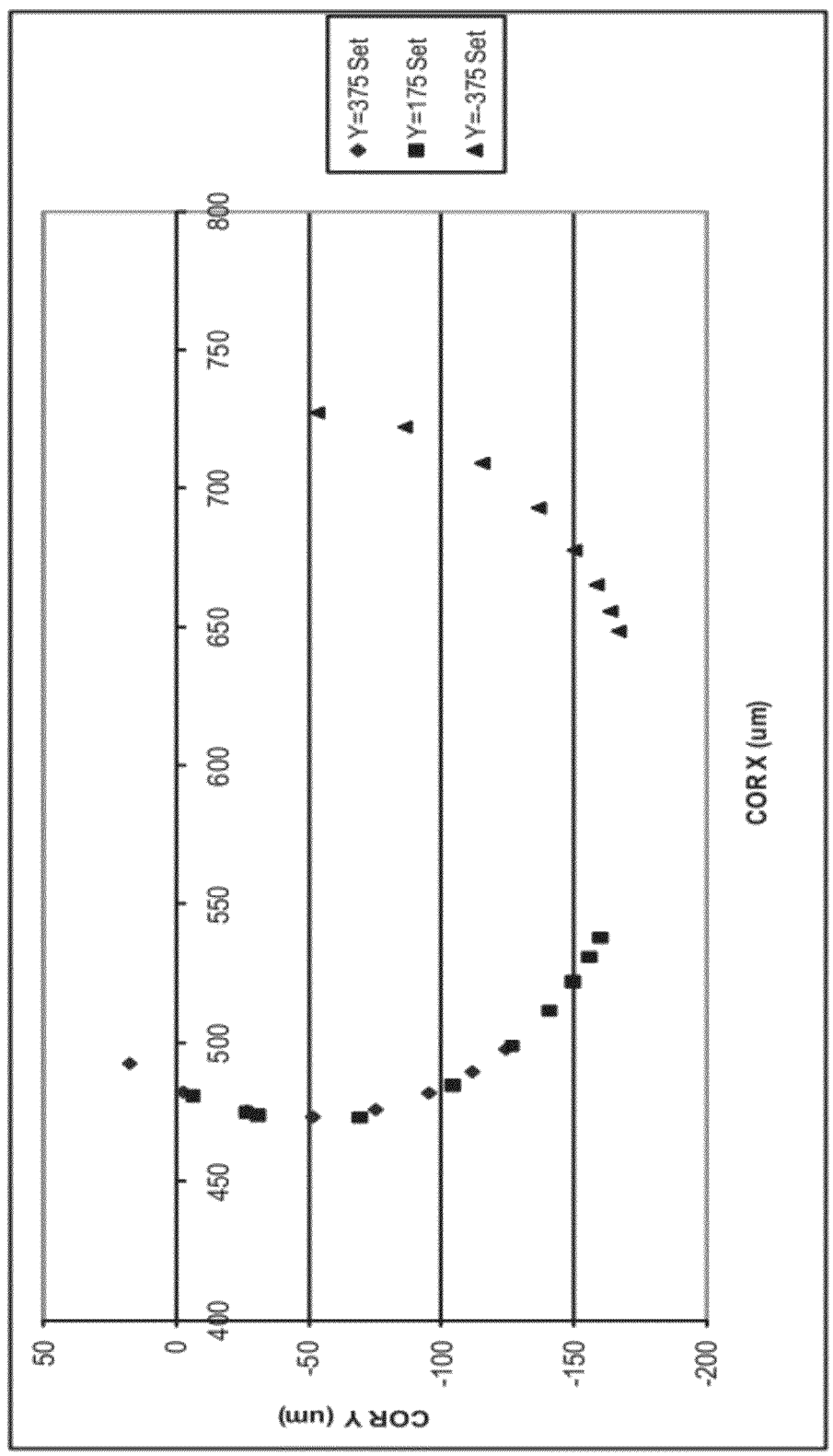
Figure 42:
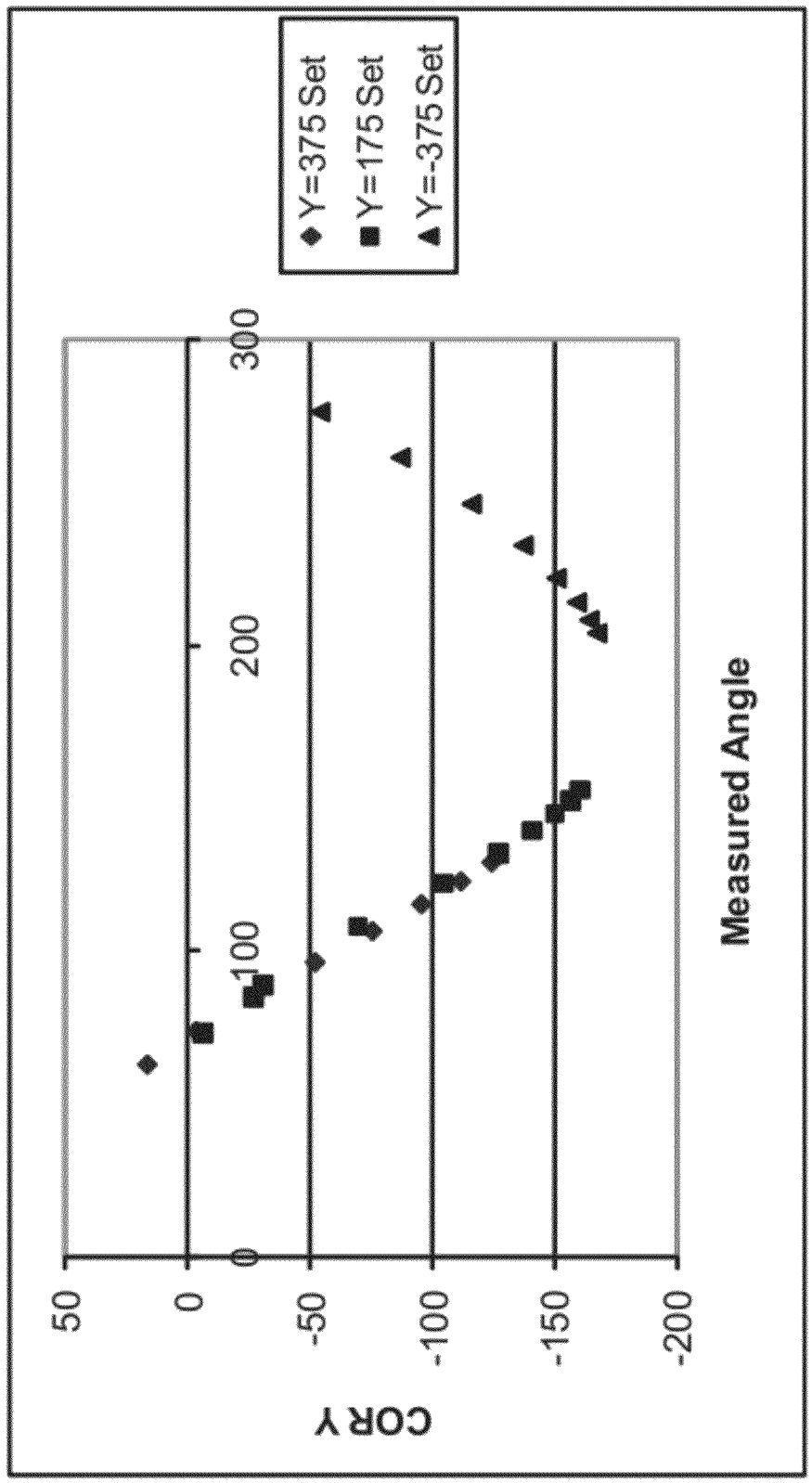
Figure 43:
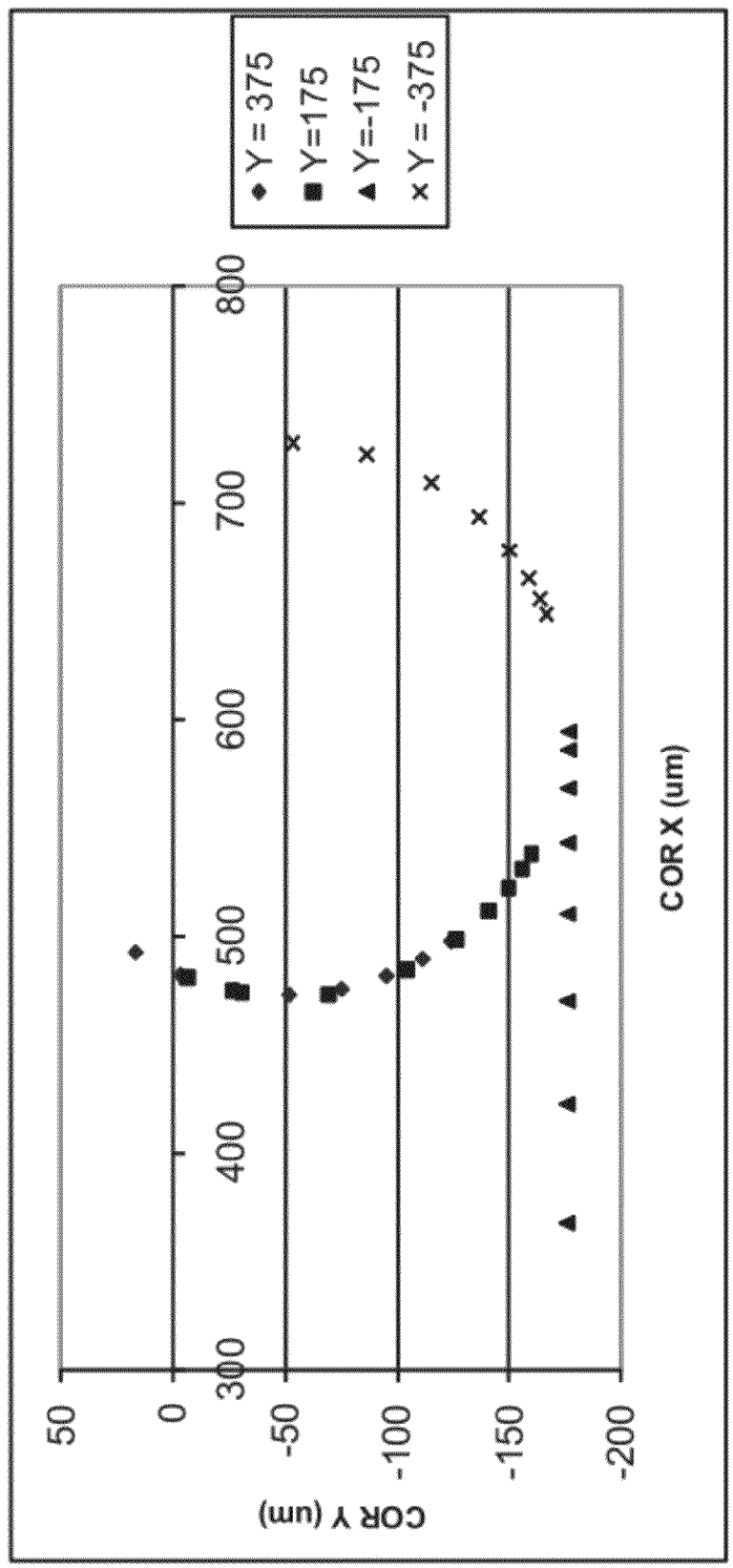
FIG. 43 illustrates a center of rotation/staring circle calculation technique, where a coordinate set Y=175 is removed from some calculations, because with a center of rotation offset of Y=−50 and an optical axis displacement of 125, the resulting set of data becomes too noisy in an X-dimension.

In embodiments, the edge imaging system 102 angle stage (scanning around the edge of the wafer) may have a rotation center point corresponding to a single value location in the shadow/edge profiler system 104 field of view. It should be noted that a square edged wafer (as seen in FIGS. 15 and 16) may provide an easy to view feature in both the edge imaging system 102 image and the shadow/edge profiler system 104 profile. Further, a radial stage may be utilized to move the edge imaging system 102 closer to wafer center, creating an opportunity for various edge locations in the horizontal shadow/edge profiler system 104 field of view. The "center" location of the edge imaging system 102 scan may thus be located on the shadow/edge profiler system 104 profile. An observed feature angle in the edge imaging system 102 scan may be intersected with the profile image.

It should be noted that the discontinuous edge 108 of the calibration wafer 106 may comprise a single flat cut to square the bevel off the wafer, which could be cut with the wafer spinning eccentrically. This may create a continuous set of angles viewable for calibration. Moreover, the calibration wafer 106 may also be cut with a flat to load for edge imaging system 102 in best focus, without requiring adjustment or causing misalignment of normal load centering mechanisms. This may allow a flat edge cut concentrically on the wafer to provide one or more varying feature locations to the edge imaging system 102 and the edge profiler system 104.

Referring now to FIGS. 18 through 29, various configurations for a calibration wafer are described in accordance with the present disclosure. In embodiments, the flat at 180 degrees theta (opposite the notch) may allow the edge imaging system 102 tool to recenter the calibration wafer 106 off the nominal center axis. This may allow for shifting of the edge in the field of view and may force the edge imaging system 102 to view targets through a wider range of phi angles. Further, in embodiments, the decentered loading may allow the phi location of the edges to span more than half of the potential angles viewed with only five facets and/or six specific angle points formed concentrically on a calibration wafer, which may allow for easier wafer fabrication and inspection.

In embodiments, the addition of a flat on the calibration wafer 106 may allow decentering with a variety of centering mechanisms, including a three-point contact centering mechanism where one of the points touches the flat. Further, the flat may be rotated along the contact point of the centering mechanism to achieve varying degrees of eccentricity in the load. In embodiments, the wafer may be loaded eccentrically to increase a number of non-degenerate data points available for calibration. It will be appreciated that while some specific wafer shapes and/or configurations are described herein and illustrated in the accompanying figures, these different shapes and configurations are provided by way of example only, and are not meant to be restrictive of the present disclosure. Thus, it should be noted that many alternatively configured wafers may be utilized with the present disclosure.

Referring now to FIGS. 30 through 38, a calibration model test is described in accordance with the present disclosure. In a specific embodiment, displacement of a side scan optical axis from a rotation axis by 125 µm at 1250 µm from a wafer surface, which is 1625 µm from a center of "Phi" rotation. An angle error of a side scan optical axis by 0.10 degrees is described. A scale error in "Phi" of one part in 1000 is described. An offset in "Phi" of 0.10 degrees is described. Finally, an error in "Phi" center of rotation by 25 µm in wafer radius and −50 µm in wafer height.

In embodiments, in order to calculate a calibration output, a table or a formula may be created over the range of measurable "Phi" for translating a measured angle into an actual angle (as seen by the profiler) and a "staring point." The actual angle may represent an angle of a line in profiler space with points that represent the measured "Side Scan" Phi angle. The "staring point" may represent a point on the line that will fix the line in profiler space. It should be noted that this point need not be a "Local Center of Rotation."

In embodiments, in order to apply the calibration, from the measured angle the "staring" angle and point may be determined (e.g., via lookup and/or calculation). Then, a "staring" line may be overlaid on the edge of the profile. Next, the intersection with the profile may be calculated. And finally, the location may be reported.

Referring generally to FIGS. 39 through 45, a calibration exercise for an offset wafer is described in accordance with the present disclosure. It should be appreciated that this exercise is intended to demonstrate the relationship of collected data and error sources to the result. In embodiments, a wafer center offset may be utilized to generate a continuum of collection points over an extended range. As shown in the modeled example, this technique may allow for direct measurement of compensations over a large measurement range, while providing continually varying data. This may allow for visiting a theta at which any point in a range may be directly measured, with redundant points at 180 degrees. Further, it may require no movement of a side scan head beyond profile collection.

First, a series of images is collected. For example, a wafer with an offset center is loaded, and a side scan image is collected. Then, edge feature traces are detected in the side scan image. Next, edge feature traces in the side scan image are utilized to determine profile sample angles. Profiles are then collected. Finally, the process is repeated to add sample points and minimize random error contribution.

Next, images are processed. For instance, measured points may be utilized to solve for "staring points" circle. With sufficient data points, the variables may be solved for directly (e.g., utilizing simultaneous equations). This technique may then be extended, by utilizing additional points, to solve for data sets and to determine a best fit and converge on a "best fit" solution. In embodiments, this process may include tests for "under-determined" and "marginally-determined" (i.e., noise gain) data. It will be appreciated that data may be collected over a sufficient range in both Phi and Phi radius (i.e., distance from Phi center of rotation) to achieve sufficient separation. Further, a "staring angle error" and a "Y center of rotation error" may be determined.

Then, a sufficient data set may be determined. For example, an edge profile may often fit a simple relationship between Phi and Phi Radius (and accordingly Phi and a Y-dimension). However, this relationship may lead to a solution that is over constrained by the profile utilized, not necessarily solving for the general case. Similarly, generating data may have the same effect. With reference to the presently described example, without sufficient overlap (i.e., mathematical overlap but not necessarily literal overlap) between the data sets at Y=375 and Y=175, there may be a fixed relationship between Phi and Phi Radius, leading to a potentially inaccurate solution.

Next, staring angle error components are described. In embodiments, the "staring angle error" may include any variations in features detected position versus the designed side scan Phi as a change in distance occurs. Further, any deterministic shifts with focus or optical distance may be combined into this compensation. It will be appreciated that if the calibration is found to require a nonlinear model, the calibration requirement may increase. However, in some embodiments, an expectation may exist that the calibration may be close to linear over the range utilized.

Regarding center of rotation and optical axis error, the following may be noted: Using data points near 90° and 270° on the center of rotation "Circle", a side scan center of rotation X-variable (SSCoRx) and Optical Axis Error may be directly determined (possibly with a small error as follows). It should be noted that increasing the number of points, varying the positions of the points, and taking repeated measurements may reduce the measurement error. It will be appreciated that at this point, the components of Optical Axis Error may not be separable. Further, Angle Error may not be separated from Offset. The Staring Angle error may be generated by adding an error (in SSCoRx) inversely proportional to the difference in "Phi Radius" (this error may be equal to a side scan center of rotation Y-variable (SSCoRy) error times the tangent of the Angle Error). In some embodiments, the contribution to SSCoRx may be reduced to insignificance, or may be determined to be insignificant, after the Staring Angle Error and SSCoRy have been determined. It should be noted that this may not be an issue if the Angle Error is small and/or the profile radius is nearly constant, but it may need to be determined over the expected measurement envelope. A "Working" SSCoRy may be determined but may be subject to similar uncertainty due to the Angle Error (Staring Angle Error). It will be appreciated that utilizing points near 180° and close to the same Phi-radius as the points used for SSCoRx may reduce this initial error. In embodiments, the procedure may include calculating SSCoR and the Optical Axis Errors utilizing sufficient measured points and repeating this in sets to converge on a best fit. Thus, the objective may be to include data near 90 degrees and 270 degrees, and points sufficiently away from these angles with nearly the same Phi Radius.

Figure 44:
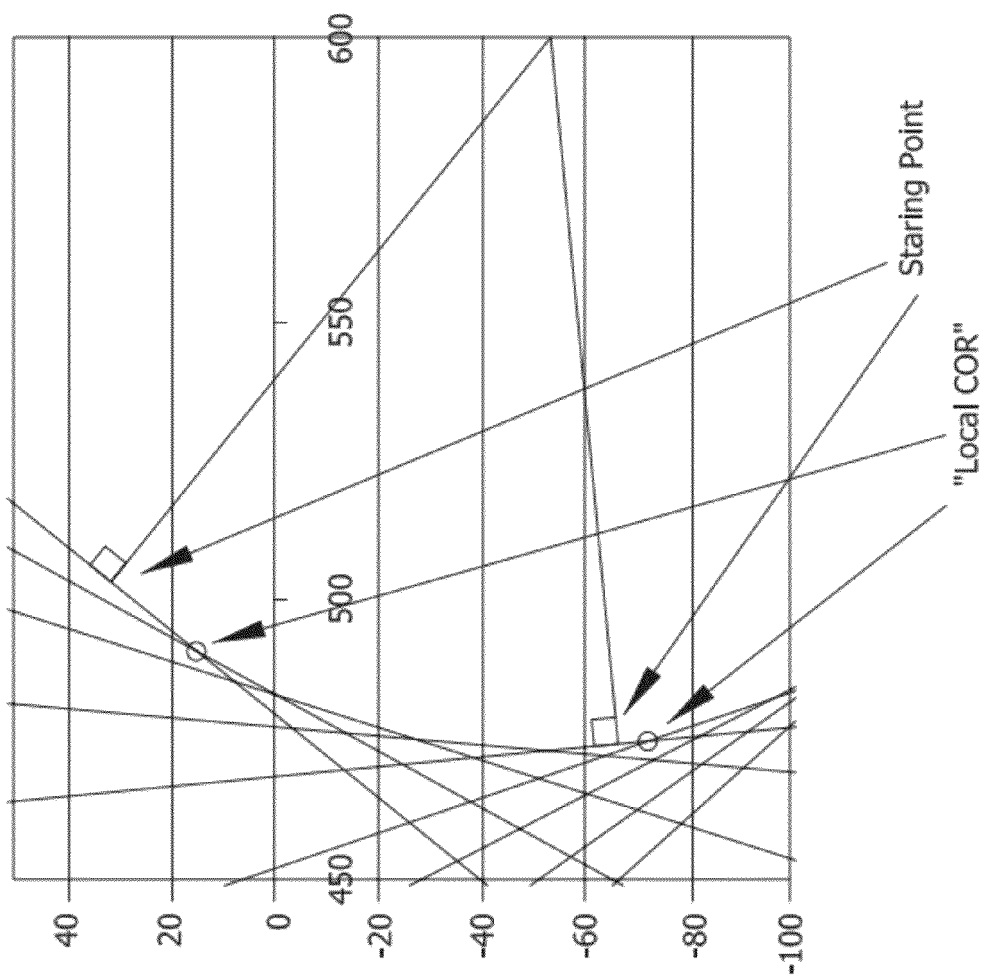
FIG. 44 illustrates finding a staring angle error.

Referring now to FIG. 44, the following may be noted: In embodiments, the effect of the Staring Angle Error is likely to be relatively small and may need to be separated. With the working SSCoR, it may be necessary to move from utilizing a local "center of rotations," which may involve intersecting line pairs, to calculating a "staring point" for each line. It will be appreciated that the staring point may be on the data line at the minimum distance from the SSCoR. Then, the Staring point radii may be examined and related to the "Phi Radius," which may yield the "Staring Angle" error.

Figure 45:
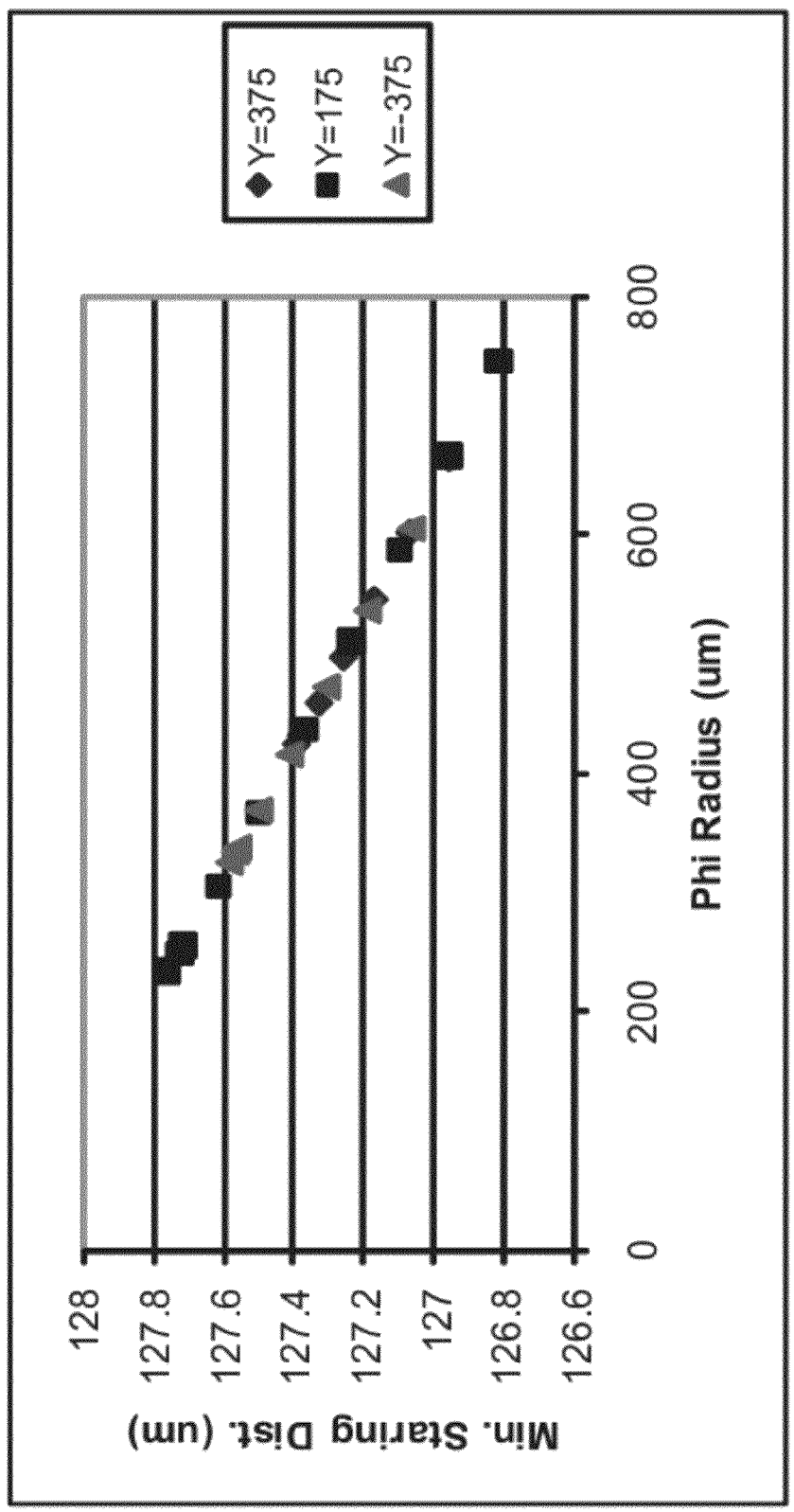
FIG. 45 illustrates a technique for finding the staring angle error, where the slope of a line is measured to find the staring angle error according to the formula staring angle error=arctangent(slope)

Referring now to FIG. 45, the following may be noted: at 0.10 degrees, the Angle Error signal may be small even from an unlikely large set of calibration data (it may not be likely to get such a range of Phi Radius). Correspondingly there may be little contribution from this small an Angle Error in the Z-Height measurement (e.g., based on a 100 µm change in Phi-Radius on a vertical section of a profile). Adding uncertainty in the data collection, determining an error to 0.1 degrees with fewer points may be marginal. For instance, between 0.13 degrees and 0.18 degrees, the error may become significant (e.g., reaching ⅓ of the total error budget; this may be based on a 100 µm change in Phi-Radius on a vertical section of a profile as previously noted). It will be appreciate that the effect may be largest near the apex and the end of the bevel. At these points, on an example profile, the "Phi-Radius" may change more with respect to Phi. In order to measure or dismiss the contribution of the angle error, a collection range exceeding any likely Phi-Radius and a significant number of measurement repeats may be required.

Figure 46:
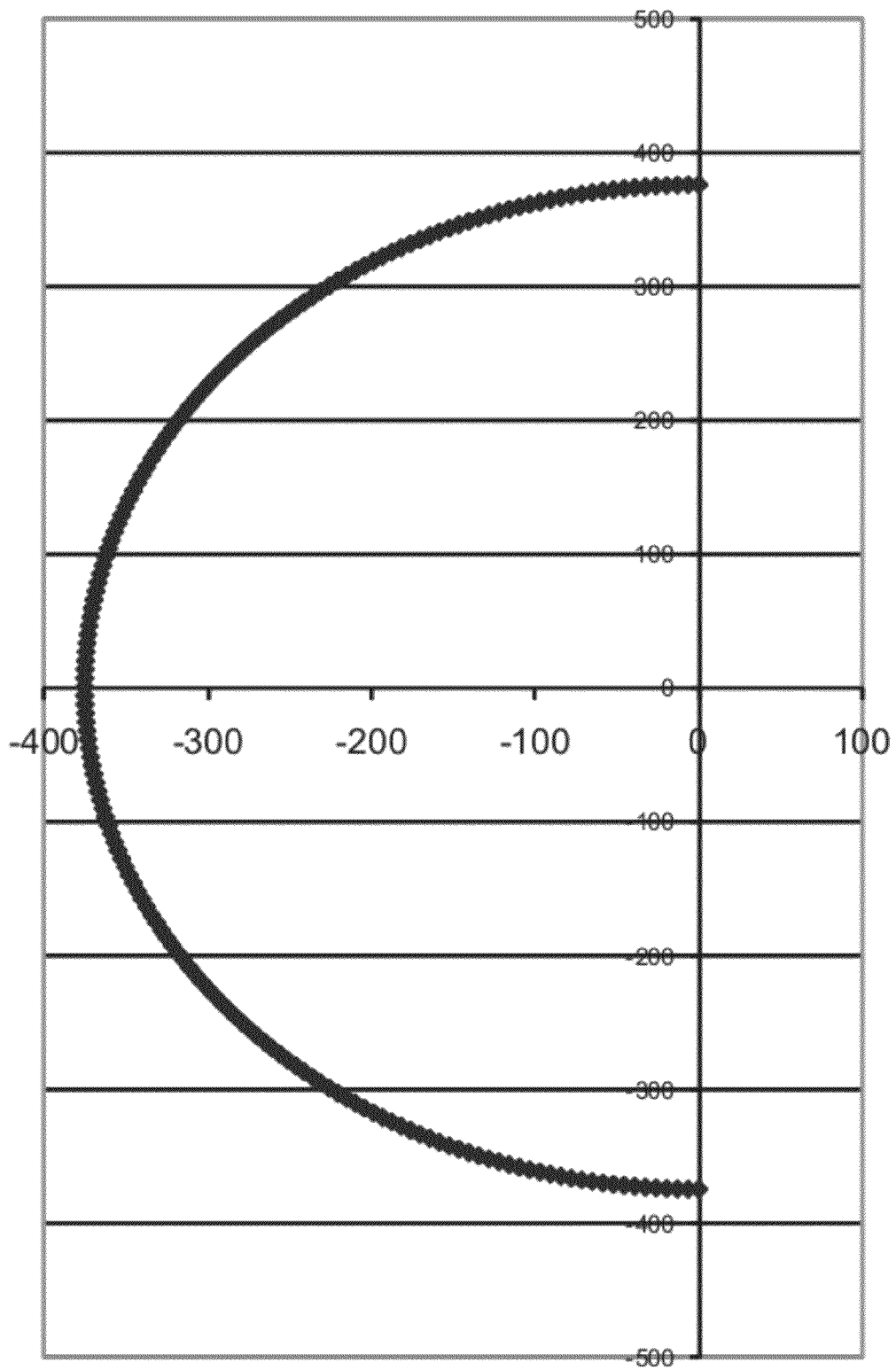
FIGS. 46 through 48 are partial side elevation view illustrating several different edge profile shapes.
Figure 47:
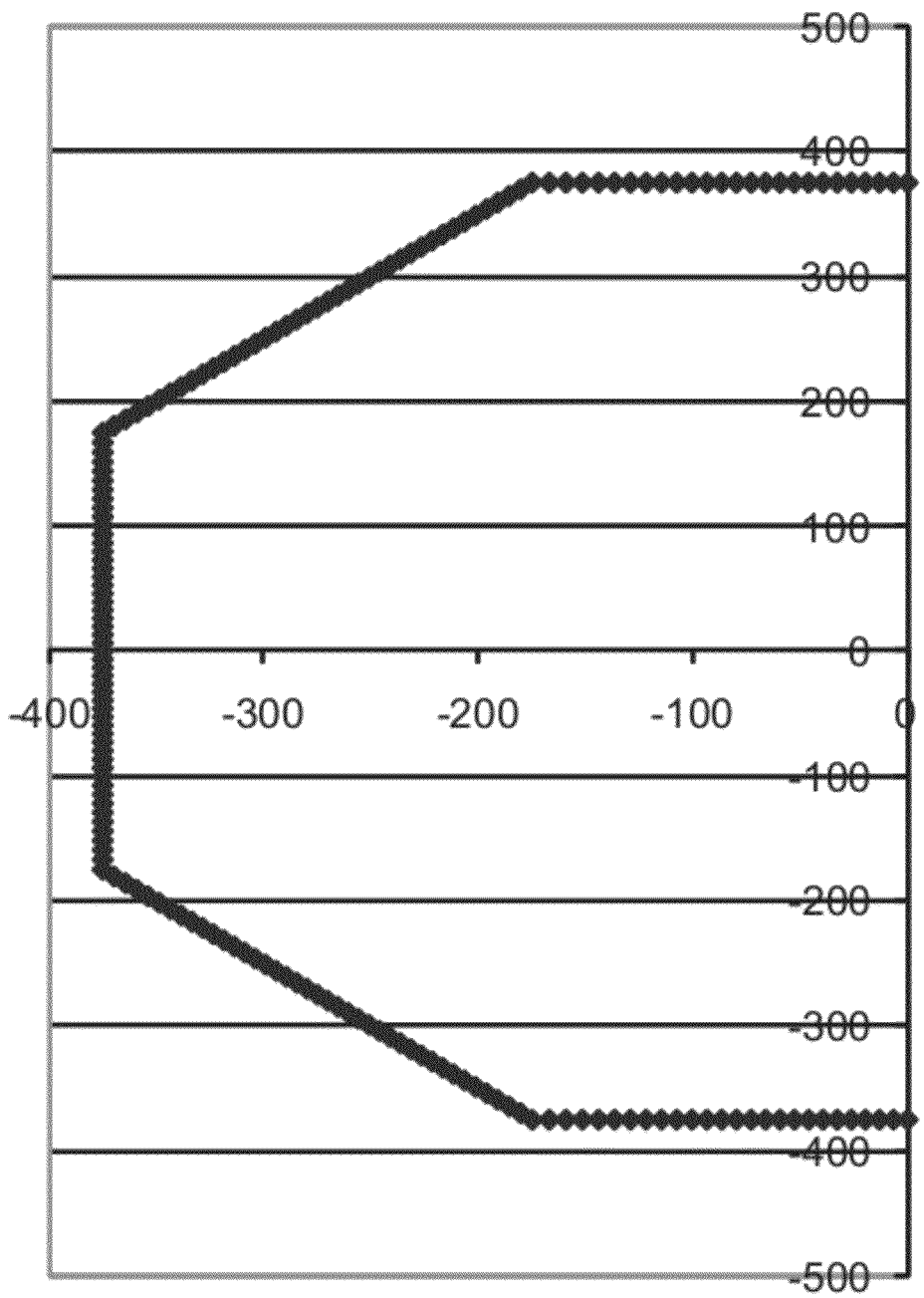
Figure 48:
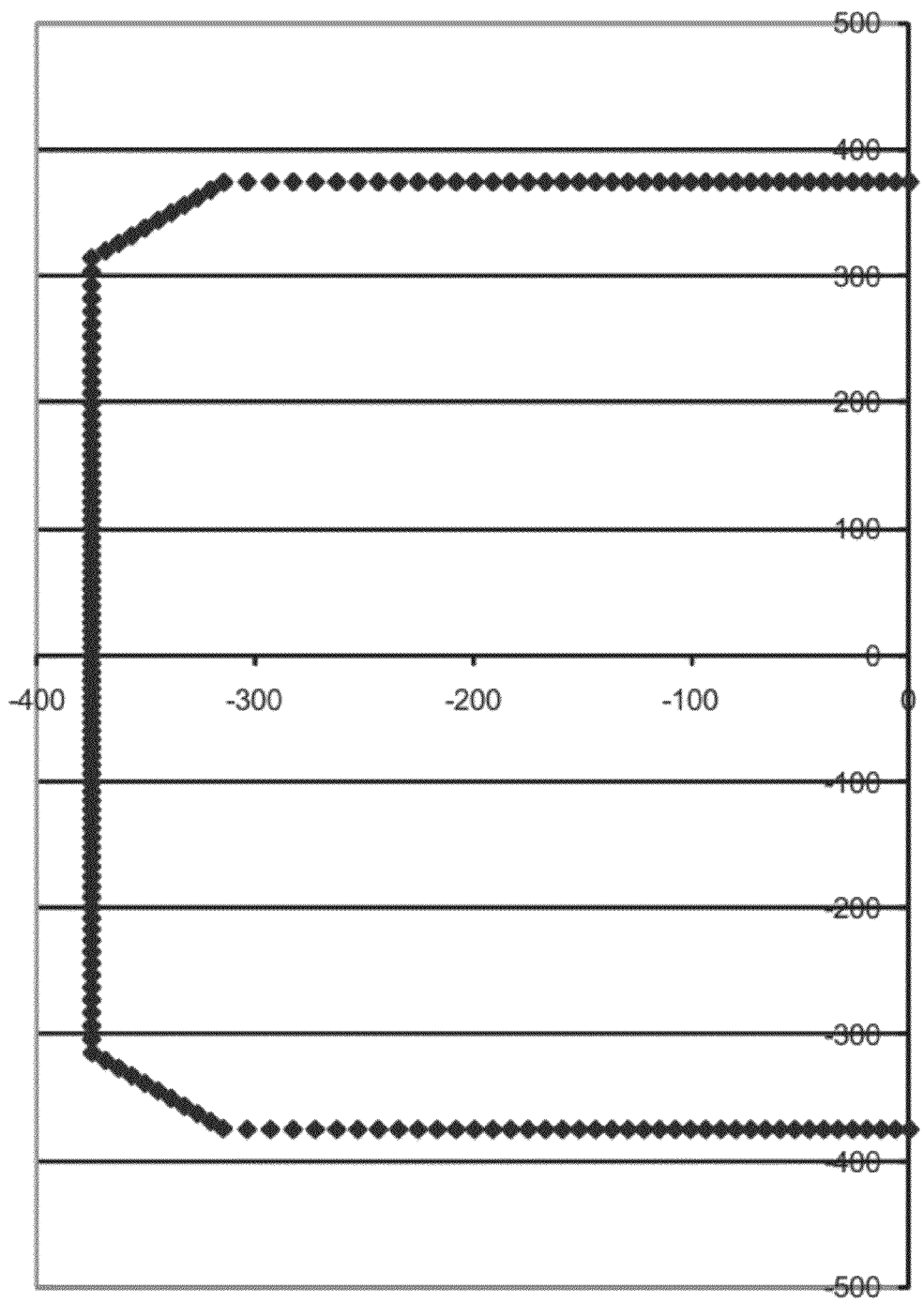
Figure 49:
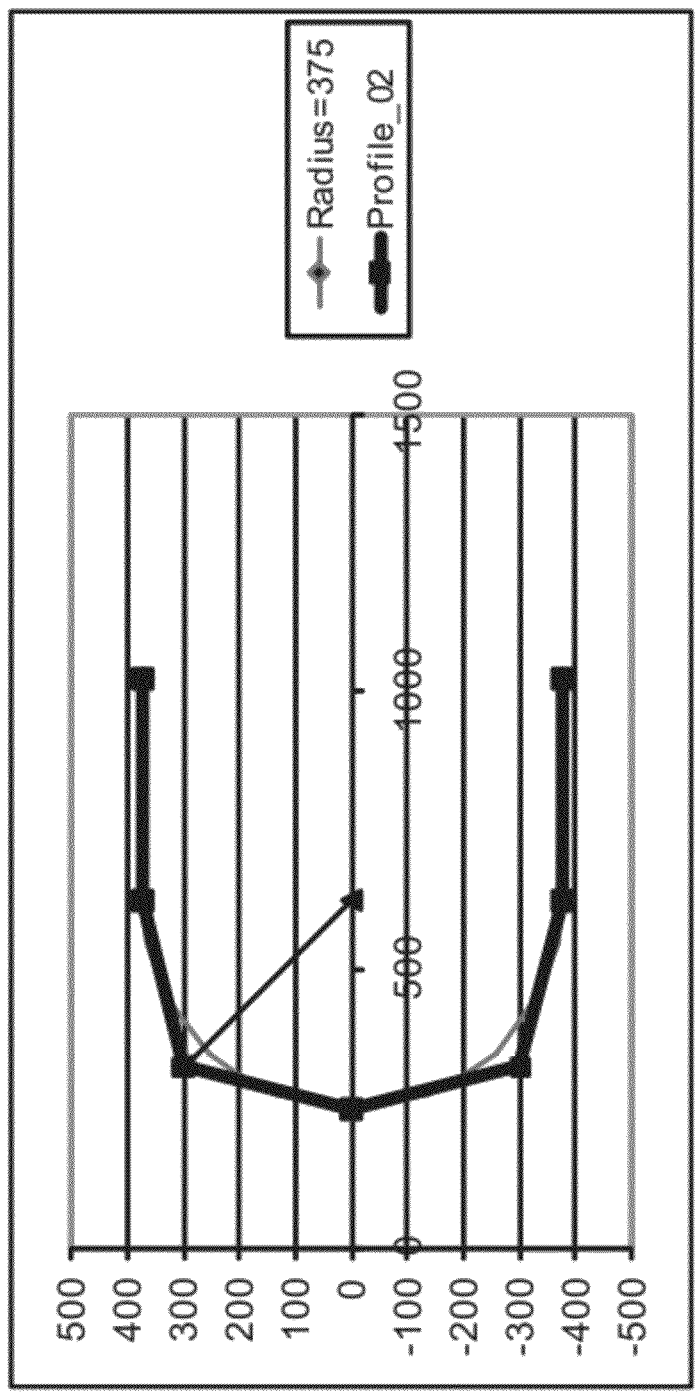
FIG. 49 is a partial side elevation view illustrating an edge profile shape for a calibration wafer.

Referring now to FIGS. 46 through 48, measurement error contribution is described in accordance with the present disclosure. In embodiments, the measurement error contribution may be derived by Monte Carlo simulation, or the like. It should be noted that conversion of coordinate error to Z-Cut may depend on a particular profile type (several profile types are illustrated in the accompanying figures). In one particular example the following condition may be present: an Optical Axis Offset may have a nominal value of at least approximately 15 µm with a range (uncertainty) of at least approximately zero. A Staring Angle Error may have a nominal value of at least approximately 0.1 degrees with a range (uncertainty) of at least approximately zero. A Center of Rotation X-value (Mainly R) may have a nominal value of at least approximately 15 µm with a range (uncertainty) of at least approximately plus-or-minus three. A Center of Rotation Y-value may have a nominal value of at least approximately 10 µm with a range (uncertainty) of at least approximately plus-or-minus 1.5. Finally, a Phi Uncertainty may have a range of at least approximately 0.045 degrees (¼ pixel in one specific embodiment). It will be appreciated that Phi Encoder Offset and Scale may be treated as common between calibration and measurement (i.e., no contribution from these).

In the presently described embodiment, a largest Z-Error may be determined between 90 and 155 degrees. For instance, a Max Sigma Z-Height (measured in µm) may be determined for a radius model (see FIG. 46) at 0.559, while being determined for the model shown in FIG. 47 at 0.692, and for the model shown in FIG. 48 at 0.916. Further, an Angle of Max Sigma (measured in degrees) may be determined for the radius model shown in FIG. 46 at 152, while being determined for the model shown in FIG. 47 at 152, and for the model shown in FIG. 48 at 141.

In order to effectively calibrate the system 100, it should be noted that data should be collected representing a sufficient range in an X-dimension, a Y-dimension, for Phi, and for "Phi Radius" in order to accurately solve for a coordinate transform. Further, the data collection may be designed to be "orthogonal" over the calculated results. For example, sample points may be taken near 90 degrees and 270 degrees (e.g., at the same radius); additional sample points may be taken closer to 180 degrees (e.g., near the same radius as the 90 degree sample points and the 270 degree sample points); and sample points may be taken at significantly different radii to provide independent measurements. Thus, it may be desirable to ensure that the data set (e.g., as a whole) may not approximate a progression where a radius could be related to Phi, X, or Y. Also, the collected data may be tested for sufficiency and cases where coupling may induce excessive "Noise Gain."

In example embodiments, a calibration wafer may be formed with clearly detectable features and/or changes in profile. The profile may benefit from a changing radius without "R-Motion", where "R-Motion" may be defined as translation of the wafer imaging device 102 in the radial direction. However, it may still be desirable to provide "R-Motion" translation (which may be intentional or otherwise) in order to yield sufficient data.

It should be noted that in an embodiment where the shadow/edge profiler system 104 is translated back and forth with respect to the calibration wafer 106, the shadow/edge profiler system 104 may be returned to a nominal radius position to calibrate a center of rotation for the calibration wafer 106. Further, it will be appreciated that the shadow/edge profiler system 104 may be moved over a range sufficient to cover more than an expected "Phi Radius" range.

In further embodiments, an EBR film printed wafer may be scanned by the edge imaging system 102. Film information may be collected in the edge imaging system scan, and a profile may be collected utilizing the shadow/edge profiler system 104. The EBR film printed wafer may then be diced and measured with an EBeam machine or other suitable coordinate measurement device in order to determine the location of the feature in the shadow/edge profiler system 104 image.

In other embodiments, a three-dimensional target (such as a five-micrometer ball or a Poly Styrene Latex (PSL) sphere) may be sprayed and/or placed on a wafer. The target may then be viewable with both the edge imaging system 102 and the shadow/edge profiler system 104.

In still further embodiments, non-wafer based target systems may be utilized. For example, a non-wafer based target may include a five-micrometer ball (e.g., constructed from PSL or nickel), which may be suspended on a structure allowing for data collection from the edge imaging system 102 and the shadow/edge profiler system 104.

In the present disclosure, the methods disclosed may be implemented as sets of instructions or software readable by a device. Further, it is understood that the specific order or hierarchy of steps in the methods disclosed are examples of exemplary approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A system, comprising:
    a support configured to rotatably support a wafer;
    an imager for generating an image by scanning a first region on an edge of a wafer, a second region on a first side of the wafer proximal to the edge of the wafer, and a third region on a second side of the wafer proximal to the edge of the wafer, where the image includes a first coordinate reference;
    a profiler for generating an edge shadow profile in a Z-direction including an apex of the edge, the profile generated by projecting at least nominally collimated light in a direction at least substantially parallel to the first side of the wafer and the second side of the wafer, the at least nominally collimated light projected past the edge of the wafer, where the profile includes a second coordinate reference; and
    control programming for locating at least one structural feature of the edge of the wafer recognizable by both the imager and the profiler for allowing the first coordinate reference to be mapped to the second coordinate reference.

2. The system of claim 1, wherein the image generated by the imager includes a first coordinate system, the profile generated by the profiler includes a second coordinate system, and the first coordinate system and the second coordinate system are boresighted.

3. The system of claim 1, wherein the edge of the wafer includes at least one of a plurality of facets, a square edge, a notch, or a flat.

4. The system of claim 1, wherein the wafer includes an offset wafer center axis to provide an apparent eccentric axis of rotation.

5. The system of claim 1, wherein the profiler is configured to translate with respect to the wafer to provide an apparent eccentric axis of rotation.

6. The system of claim 1, wherein the edge of the wafer includes a three-dimensional target viewable by both the imager and the profiler.

7. The system of claim 1, further comprising a non-wafer based target suspended in view of both the imager and the profiler, where the control programming is configured for locating the non-wafer based target and allowing additional coordinate references generated by the imager and the profiler for the non-wafer based target to be mapped to one another.

8. A method, comprising:
    rotatably supporting a wafer;
    generating an image of the wafer by scanning a first region on an edge of the wafer, a second region on a first side of the wafer proximal to the edge of the wafer, and a third region on a second side of the wafer proximal to the edge of the wafer, where the image includes a first coordinate reference;
    generating an edge shadow profile of the wafer by projecting at least nominally collimated light in a direction at least substantially parallel to the first side of the wafer and the second side of the wafer, and obtaining a profile image in a Z-direction including an apex of the edge, the at least nominally collimated light projected past the edge of the wafer, where the edge shadow profile includes a second coordinate reference;
    locating at least one structural feature of the edge of the wafer on both the image and the profile; and
    mapping the first coordinate reference to the second coordinate reference utilizing the at least one structural feature of the edge of the wafer.

9. The method of claim 8, further comprising:
    boresighting a first coordinate system of the image and a second coordinate system of the profile.

10. The method of claim 8, wherein the edge of the wafer includes at least one of a plurality of facets, a square edge, a notch, or a flat.

11. The method of claim 8, wherein the wafer includes an offset wafer center axis to provide an apparent eccentric axis of rotation.

12. The method of claim 8, further comprising:
    translating the profiler with respect to the wafer to provide an apparent eccentric axis of rotation.

13. The method of claim 8, wherein the edge of the wafer includes a three-dimensional target viewable by both the imager and the profiler.

14. The method of claim 8, further comprising:
    suspending a non-wafer based target in view of both the imager and the profiler;
    locating the non-wafer based target on both the image and the edge shadow profile to generate additional coordinate references; and
    mapping the additional coordinate references generated by the imager and the profiler to one another.

15. An apparatus, comprising:
    a wafer having a discontinuous edge;
    an imager for generating an image of the wafer by scanning a first region on an edge of the wafer, a second region on a first side of the wafer proximal to the edge of the wafer, and a third region on a second side of the wafer proximal to the edge of the wafer, where the image generated by the imager includes a first coordinate system;

a profiler for generating an edge profile of the wafer by projecting at least nominally collimated light in a direction at least substantially parallel to the first side of the wafer and the second side of the wafer and obtaining a profile image in a Z-direction including an apex of the edge, the at least nominally collimated light projected past the edge of the wafer, where the edge profile generated by the profiler includes a second coordinate system; and control programming for locating at least one structural feature of the discontinuous edge of the wafer recognizable by both the imager and the profiler for allowing the first coordinate system to be mapped to the second coordinate system.

16. The system of claim 1, wherein the first coordinate system and the second coordinate system are boresighted.

17. The system of claim 1, wherein the discontinuous edge of the wafer includes at least one of a plurality of facets, a square edge, a notch, or a flat.

18. The system of claim 1, wherein the wafer includes an offset wafer center axis to provide an apparent eccentric axis of rotation.

19. The system of claim 1, wherein the profiler is configured to translate with respect to the wafer to provide an apparent eccentric axis of rotation.

20. The system of claim 1, wherein the discontinuous edge of the wafer includes a three-dimensional target viewable by both the imager and the profiler.

* * * * *